US011618031B2

(12) United States Patent
Sozzani et al.

(10) Patent No.: US 11,618,031 B2
(45) Date of Patent: Apr. 4, 2023

(54) MULTI-SAMPLE CHAMBER FOR EXTENDED TERM MICROSCOPE IMAGING

(71) Applicant: North Carolina State University, Raleigh, NC (US)

(72) Inventors: Rosangela Sozzani, Raleigh, NC (US); Timothy J. Horn, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 532 days.

(21) Appl. No.: 16/461,645

(22) PCT Filed: Nov. 14, 2017

(86) PCT No.: PCT/US2017/061424
§ 371 (c)(1),
(2) Date: May 16, 2019

(87) PCT Pub. No.: WO2018/093740
PCT Pub. Date: May 24, 2018

(65) Prior Publication Data
US 2019/0351423 A1    Nov. 21, 2019

Related U.S. Application Data

(60) Provisional application No. 62/423,935, filed on Nov. 18, 2016.

(51) Int. Cl.
*G02B 21/26* (2006.01)
*G02B 21/34* (2006.01)
(Continued)

(52) U.S. Cl.
CPC ............... *B01L 9/06* (2013.01); *C12M 23/48* (2013.01); *C12M 41/36* (2013.01); *G02B 21/16* (2013.01);
(Continued)

(58) Field of Classification Search
CPC ........ G02B 21/00; G02B 21/34; G02B 21/16; G02B 21/26; C12M 23/48; C12M 41/36; B01L 9/06
(Continued)

(56) References Cited

U.S. PATENT DOCUMENTS 3,331,665 A    7/1967 Natelson
3,824,841 A    7/1974 Bull
(Continued)

FOREIGN PATENT DOCUMENTS

JP    63-257172    * 10/1988

OTHER PUBLICATIONS

International Search Report and Written Opinion for PCT/US2017/061424 dated Feb. 2, 2018.

*Primary Examiner* — Thong Q Nguyen
(74) *Attorney, Agent, or Firm* — Thomas|Horstemeyer, LLP

(57) ABSTRACT

Provided is a biological specimen holder for positioning multiple specimens for imaging by a light-sheet microscope. The specimen holder allows developing plant embryos, small intact animals, or organs to be imaged in the light-sheet microscope in a single setting. The specimen holders significantly improve the imaging conditions with respect to the standard glass capillary system. Also provided is a semi-automatic image processing pipeline that quantifies cell divisions of plants imaged with both the glass capillary and the novel chambers. Plants imaged using the specimen holder undergo cell divisions for a period at least 16 times longer than those imaged with a glass capillary system and allow increased sample throughput and the option of incorporating light emitting diode (LED) lights to generate a light-controlled environment are also advantages.

8 Claims, 19 Drawing Sheets

(51) Int. Cl.
*B01L 9/06* (2006.01)
*C12M 3/00* (2006.01)
*C12M 1/34* (2006.01)
*G02B 21/16* (2006.01)

(52) U.S. Cl.
CPC .............. *G02B 21/26* (2013.01); *G02B 21/34* (2013.01); *B01L 2300/041* (2013.01); *B01L 2300/0803* (2013.01); *B01L 2300/0851* (2013.01)

(58) Field of Classification Search
USPC .......................................... 359/368, 391–398
See application file for complete search history.

(56) References Cited

U.S. PATENT DOCUMENTS

| | | | | |
|---|---|---|---|---|
| 5,594,164 | A | * | 1/1997 | Bull ...................... G01N 15/05 356/246 |
| 5,982,535 | A | * | 11/1999 | Inoue ..................... G02B 21/26 359/368 |
| 8,519,358 | B2 | * | 8/2013 | Ingber ................. G01N 21/0303 356/246 |
| 2006/0286619 | A1 | | 12/2006 | Ricci et al. |
| 2010/0067104 | A1 | | 3/2010 | Lippert et al. |
| 2012/0245013 | A1 | | 9/2012 | Alomair |
| 2015/0375340 | A1 | | 12/2015 | Cui et al. |

\* cited by examiner

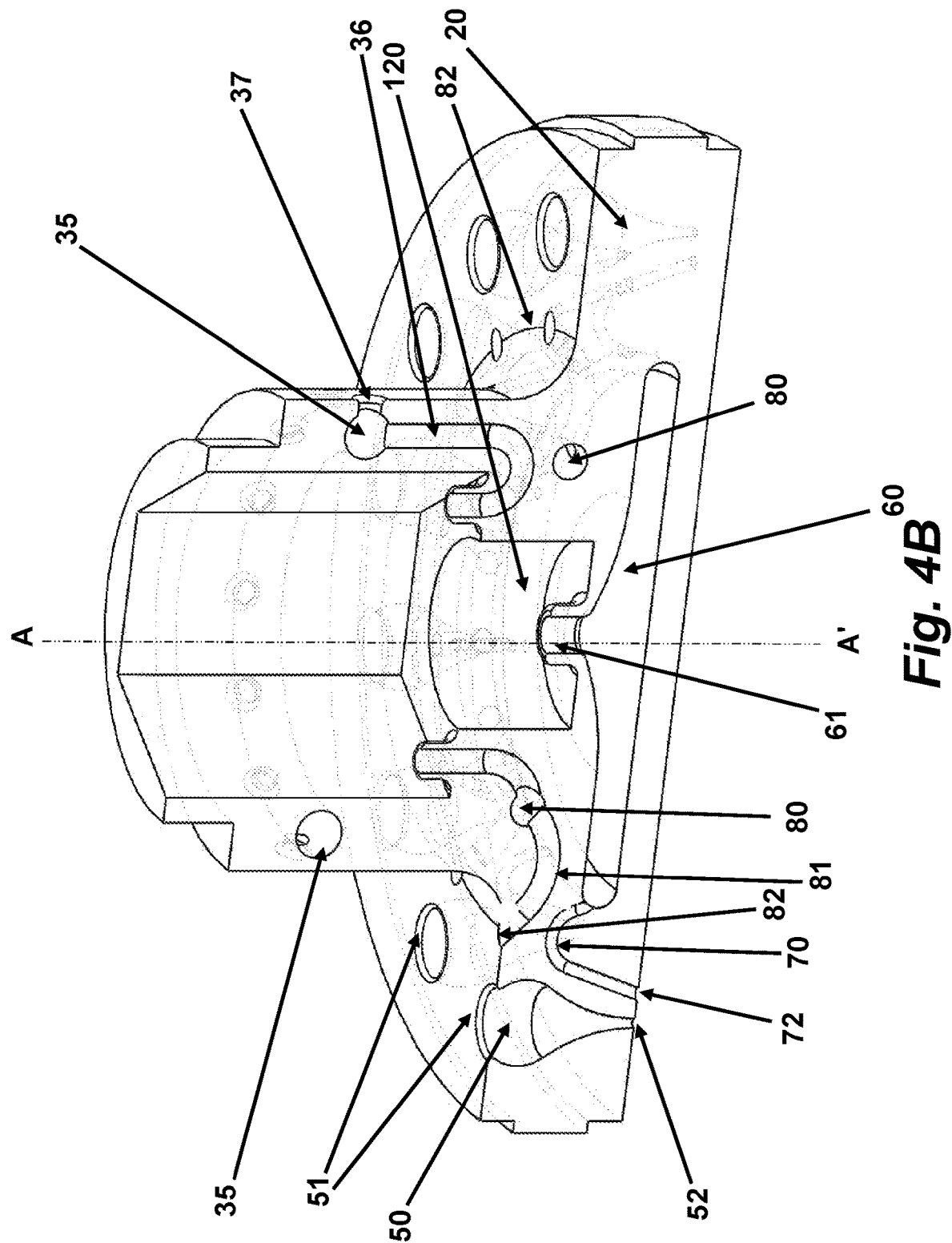

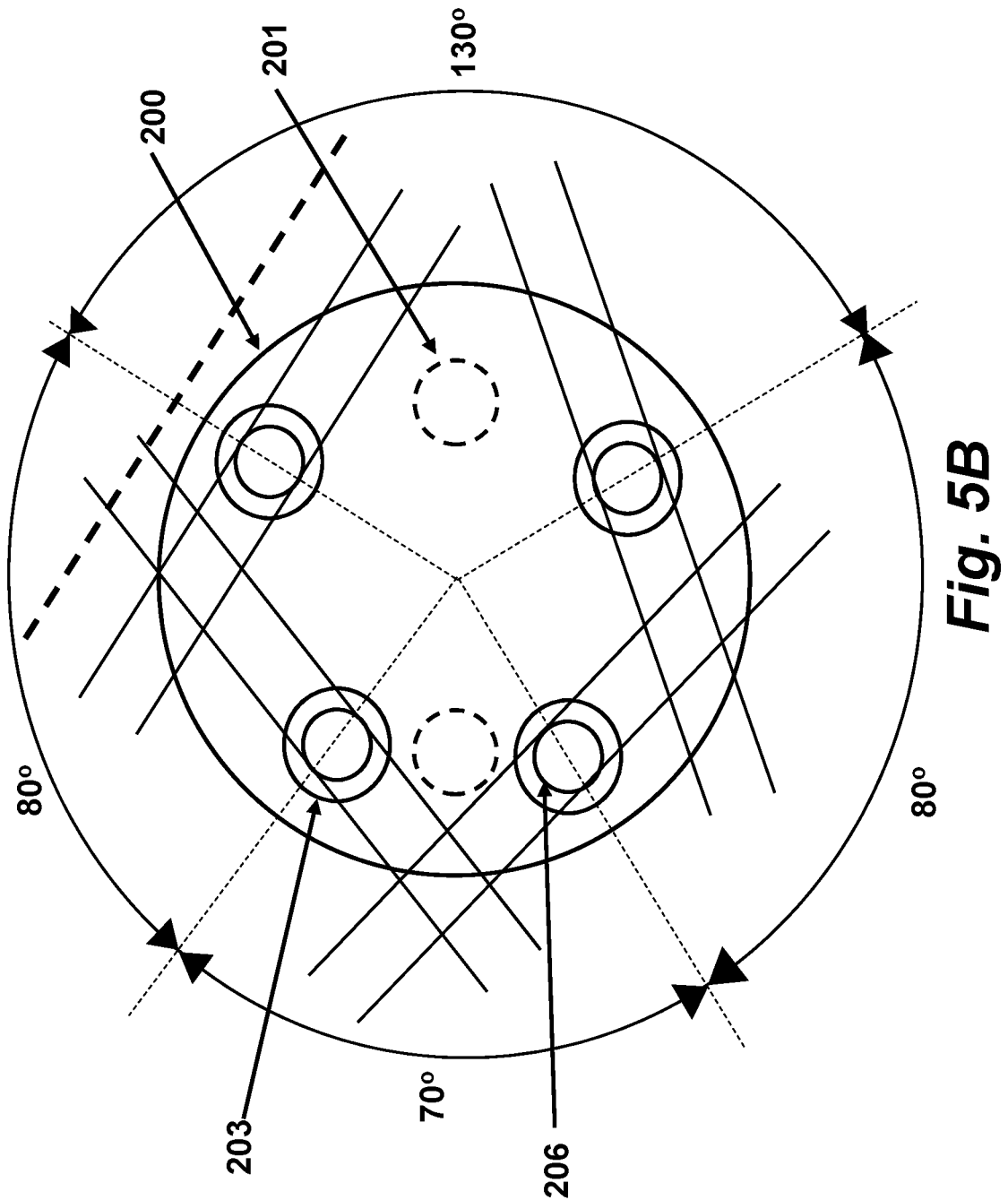

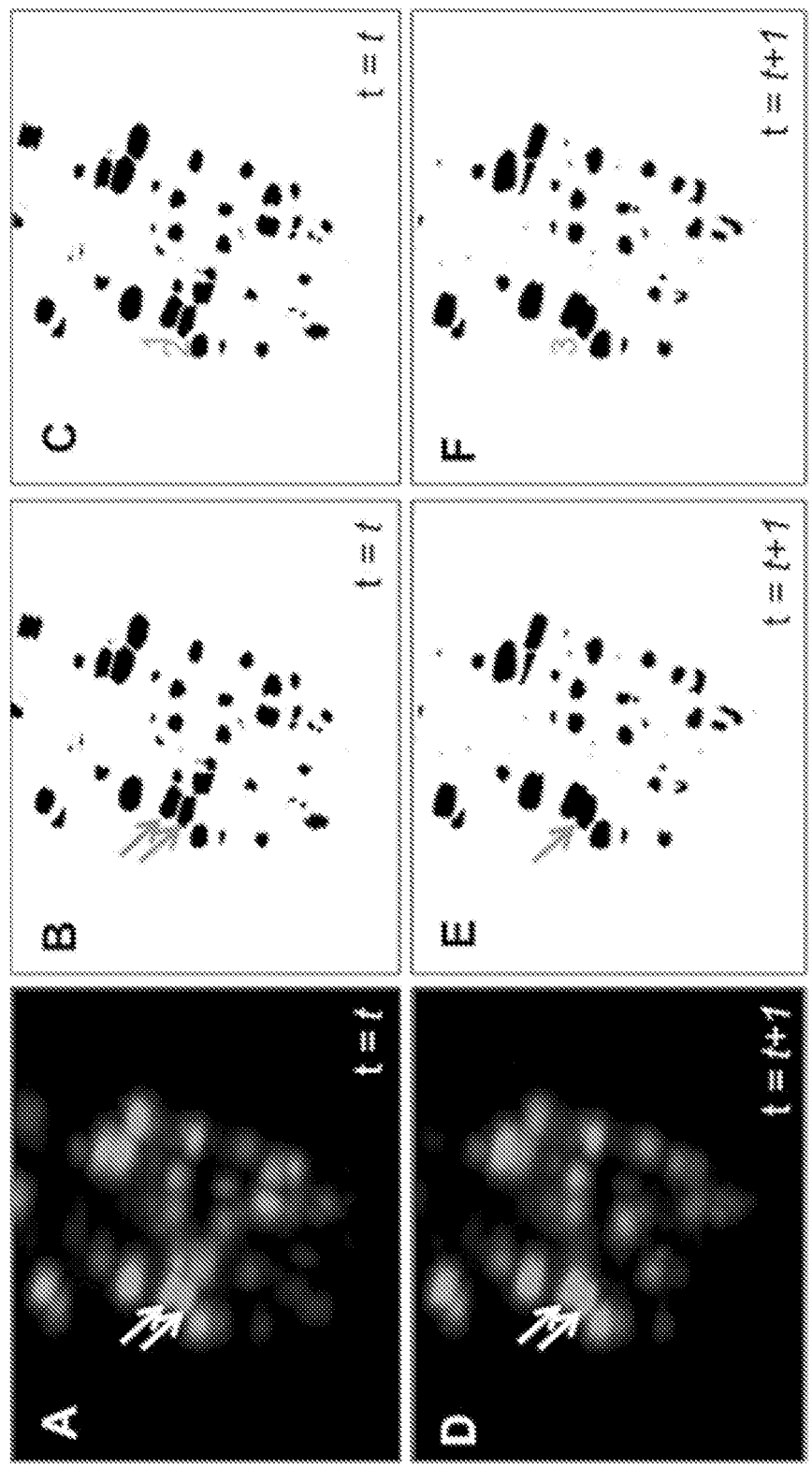

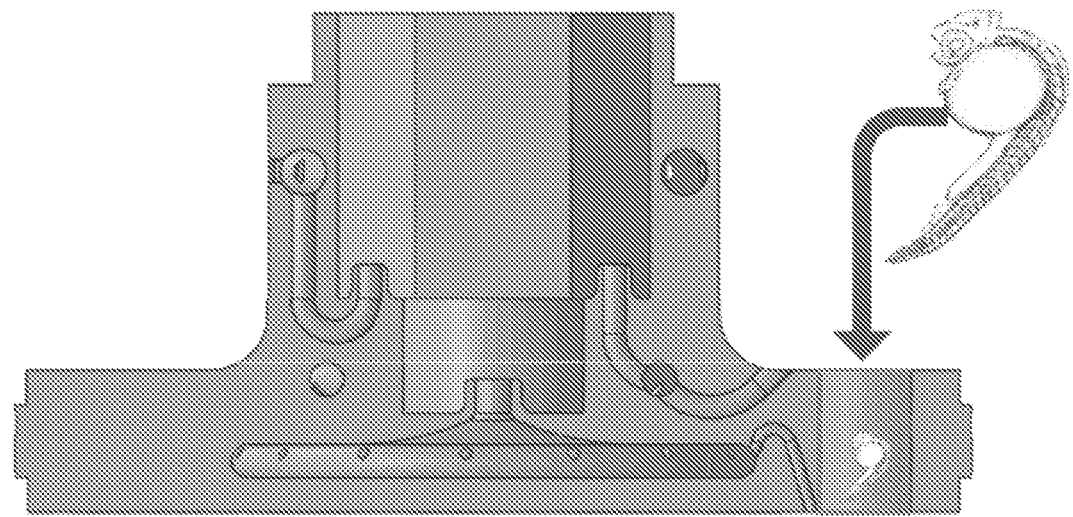
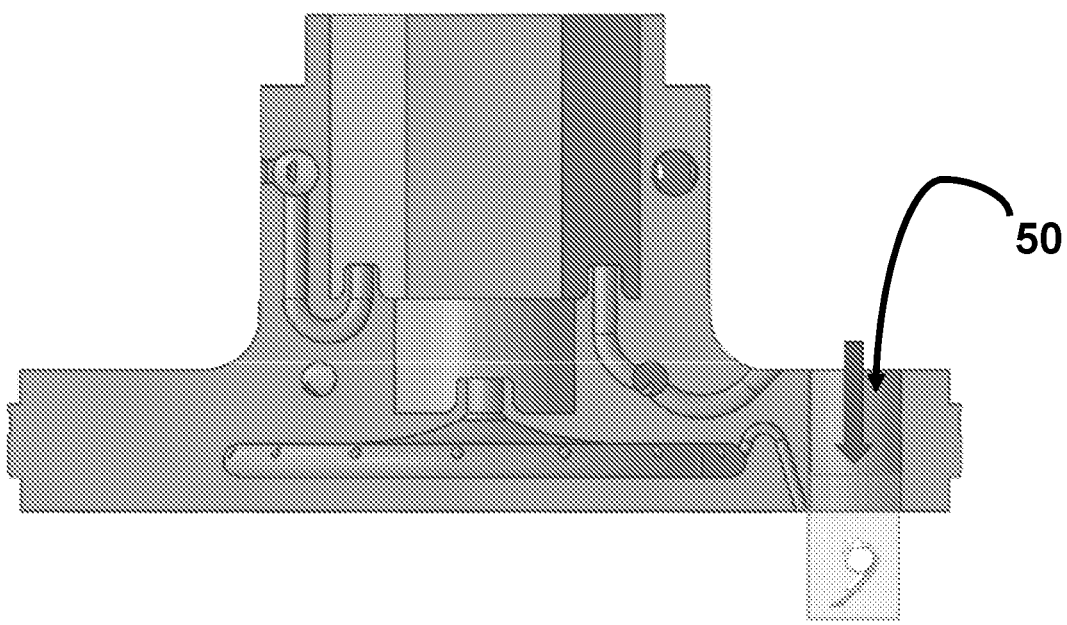
*Fig.12*

MULTI-SAMPLE CHAMBER FOR EXTENDED TERM MICROSCOPE IMAGING

CROSS-REFERENCE TO RELATED APPLICATIONS

This application is the 35 U.S.C. 371 national stage application of PCT Application No. PCT/US2017/061424, filed on Nov. 14, 2017, where the PCT claims priority benefit of U.S. Provisional Patent Application Ser. No. 62/423,935 filed on Nov. 18, 2016 and titled "MULTI-SAMPLE CHAMBER FOR EXTENDED TERM MICROSCOPE IMAGING" the entire disclosure disclosures of which are herein incorporated by reference in their entireties.

STATEMENT ON FUNDING PROVIDED BY THE U.S. GOVERNMENT

This invention was made with government support under grant numbers 1453130 and 1517058 awarded by the National Science Foundation. The government has certain rights to this invention.

TECHNICAL FIELD

The present disclosure is generally related to a mount for loading multiple biological samples into a light-sheet microscope.

BACKGROUND

Understanding the dynamics underlying plant growth requires quantitative analyses of the organism's development over time. A key strategy to perform quantitative analyses of plant development over time is the observation of spatiotemporal cues in in vivo specimens (Reynaud et al., (2008) *HFSP J.* 2: 266-275). Confocal laser scanning microscopy, spinning disc microscopy, and epifluorescence platforms have been typically used to study such developmental cues through the visualization of fluorescently tagged proteins, individual cells, and tissue types at specific developmental stages (Ovečka, et al., (2105) *Nat. Protoc.* 10: 1234-1247). However, photo-induced cellular toxicity and fluorophore bleaching impose severe time limitations on the use of these microscopy tools (Sena et al., (2011) *PLoS One* 6: 1-11). Consequently, the use of these tools is generally limited to imaging developmental processes that occur in short time-span intervals of seconds to minutes (von Wangenheim et al., (2014) *Methods Mol. Biol.* 1062: 539-550), although microfluidics devices have been developed that have allowed longer imaging experiments (Grossmann, et al., (2011) *Plant Cell Online* 23: 4234-4240; Busch, et al., (2012) *Nat. Methods* 9: 1101-1106).

A technical advance has been achieved with the use of light sheet fluorescence microscopy (LSFM). In LSFM, the sheet of light that illuminates the specimen is orthogonal to the detection path (Maizel et al., (2011) *Plant J.* 68: 377-385) and only fluorophores close to the focal plane of the detection system contribute to potential phototoxicity (Reynaud et al., (2008) *HFSP J.* 2: 266-275). By reducing photobleaching effects while imaging, the specimen is exposed to 5000 times less energy than in a confocal microscope (von Wangenheim et al., (2014) *Methods Mol. Biol.* 1062: 539-550). Furthermore, the light sheet, particularly in the Zeiss Z.1 microscope, has a unique stage set up suited for imaging plant organisms. The specimen is suspended vertically, which allows for roots to follow the gravity vector. The light sheet stage allows for 3-dimensional movement and rotation around a vertical axis, such that imaging from all angles is possible (Reynaud et al., (2008) *HFSP J.* 2: 266-275). Additionally, data acquisition in LSFM technology allows the detector to collect all pixels in one image as opposed to one pixel at a time, which has a great impact on the rate of image acquisition (100 frames per second) in contrast to the confocal at 1-5 frames per second (Reynaud et al., (2008) *HFSP J.* 2: 266-275; Weber & Huisken (2011) *Curr. Opin. Genet. Dev.* 21: 566-572). As a result, LSFM permits lengthier imaging time course experiments than conventional microscopes and possesses unique characteristics well-suited for imaging plants. Accordingly, LSFM has been used to study longer developmental events such as plant organogenesis and lateral root formation (Sena et al., (2011) *PLoS One* 6: 1-11; Maizel et al., (2011) *Plant J.* 68: 377-385, Vermeer, et al. (2014) *Science,* 343: 178-183; Vermeer & Geldner (2015) *F1000Prime Rep.* 7: 32).

Although LSFM overcomes multiple long-term imaging issues, certain challenges remain when imaging plants. First, only one specimen can be imaged at a time, preventing the imaging process from scaling up. This becomes a limiting factor for long-term experiments, where obtaining biological replicates significantly increases time and economic costs. Second, the specimen to be imaged needs to be transferred and loaded from its original growing plate into an imaging capillary system, which can be time-consuming and can generate a stress response in the plant. Moreover, when loaded in the capillary system provided by ZEISS for imaging, both shoot and root are embedded in agar. This prevents the shoot from exchanging gases, thereby inducing an extreme, rapid stress response in the plant. Although previous protocols have addressed the drawback of transferring plants to a glass capillary or having the shoot embedded in agar (Ovečka, et al., (2105) *Nat. Protoc.* 10: 1234-1247; Sena et al., (2011) *PLoS One* 6: 1-11; von Wangenheim et al., (2014) *Methods Mol. Biol.* 1062: 539-550; Maizel et al., (2011) *Plant J.* 68: 377-385; Novak et al., (2015) *Front. Plant Sci.* 6: 1187), no attempt has been made to scale-up the number of plants imaged in the same experiment.

SUMMARY

Provided are embodiments of a biological specimen holder for positioning multiple specimens to be imaged in a light-sheet microscope. The embodiments of the specimen holder of the disclosure allow developing plant embryos, small intact animals, or organs to be imaged in the light-sheet microscope in a single setting. Despite the limitation that plants are maintained in the dark during the imaging session, which slows down cell divisions during extended time-course experiments, the specimen holders significantly improve the imaging conditions with respect to the standard glass capillary system. Also provided is a semi-automatic image processing pipeline that quantifies cell divisions of plants imaged with both the glass capillary and the novel chambers. Plants imaged using the holders of the disclosure undergo cell divisions for a period at least 16 times longer than those imaged with the glass capillary system and allow for increased sample throughput and the option of incorporating light emitting diode (LED) lights to generate a light-controlled environment are also advantages.

Accordingly, one aspect of the disclosure provides embodiments of a biological specimen holder comprising: a sample receiving disc having a top surface and a bottom surface, wherein said top surface has attached thereto a co-axial drive shaft receiving tube or a co-axial indent configured to receive an end of a drive shaft; a bottom supporting disc having a top surface and a bottom surface; at least two supporting rods, one end of each of the supporting rods being attached to the bottom surface of the sample receiving disc and the opposing ends of the supporting rods being attached to the top surface of the bottom supporting disc; wherein the sample receiving disc has a plurality of sample tube receiving perforations located in the sample receiving disc such that only a single biological specimen can be illuminated by a light-sheet beam when the biological specimen holder is in a light-sheet microscope.

Another aspect of the disclosure provides embodiments of a biological specimen holder comprising (a) a sample receiving disc having: a top surface with a co-axial tubular extension having an inner wall defining a co-axial lumen configured for receiving an end of a drive shaft and an annular shelf; a bottom surface; and a rim having a co-axial annular extension defining a top shelf and a bottom shelf; (b) a removable top cover comprising a top plate having a circular wall descending therefrom, said top plate including a co-axial perforation for receiving the tubular extension, wherein the circular wall engages with the annular top shelf of the annular rim extension and the top plate engages with the annular shelf of the tubular extension, the inner surface of the top cover, the top surface of the sample receiving disc, and the outer surface of the tubular extension defining a top chamber; and (c) a removable mold engaging with the bottom annular ridge of the annular rim extension the inner surface of the removable mold and the bottom surface of the sample receiving disc and defining a bottom chamber; wherein the sample receiving disc further comprises: (i) at least three traversing specimen receiving chambers, each of said chambers independently having a top opening in the top surface of the sample receiving disc and a bottom opening in the bottom surface of the sample receiving disc, and wherein each specimen receiving chamber is located within the disc such that no two chambers are diametrically opposed to each other; (ii) a liquid exchange inlet mixing chamber embedded within the sample receiving disc and communicating with the co-axial lumen of the extension through a projecting liquid exchange inlet connector; and (iii) a plurality of liquid delivery ducts extending from the liquid exchange inlet mixing chamber, each of said liquid delivery ducts having an inlet port communicating with the inlet mixing chamber and a liquid exchange inlet in the bottom surface of the sample receiving disc; wherein the tubular extension defines an internal circular outlet duct having a plurality of gas exchange outlet ports disposed to opening into the top chamber and a gas outlet duct operably communicating with the outlet duct and having a second port operably communicating with the lumen of the tubular extension via a gas exchange outlet connector projecting into the lumen, and an annular gas duct comprising a plurality of gas delivery ducts operably communicating with said annular gas duct and the top chamber, each gas delivery duct having an inlet port communicating the top surface of the disc, and a gas inlet duct projecting into the lumen of the tubular extension via a gas exchange inlet connector.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 4B is an isometric vertical section view through an embodiment of a specimen holder of the disclosure (top 4 and bottom 5 covers and the drive shaft 110 are not shown) and wherein the tubular extension is configured to receive a drive shaft having a hexagonal proximal end.

FIG. 5B is a plan of the positioning of four specimen tubes in one embodiment of a specimen holder according to the disclosure. The two parallel lines around each sample tube 206 indicate the range of motion of the light sheet when doing a z-stack. The dashed line indicates the plane of the front lens of a microscope objective perpendicular to the orthogonal plane of the illuminating light-sheet. Holes are positioned in such a way that neither the plants nor the supports obstruct the light path during imaging.

FIG. 8 illustrates the Max-projection of one root of *Arabidopsis* expressing pCYCB1;1:CYCB1;1-GFP at two consecutive time points obtained with the MAGIC specimen holder. Arrows illustrate how errors in tracking cell divisions (false positive) are introduced during the image analysis. Panel A: Max-projection of the root at time t. The arrows highlight two adjacent fluorescent cells. Panel B: Max-projection from panel A after thresholding and watershedding. The arrows point to two adjacent fluorescent cells identified by the tracking pipeline as two different objects. Panel C: Numbers represent the count of MTrack2 associated with the two fluorescent cells, 1 and 2, at time t. Panel D: Max-projection of the root at time t+1. The arrows point to the same adjacent cells as in A. Panel E: Max-projection from panel D after thresholding and watershedding. The arrow points to a cell that the tracking algorithm fails to separate into the two cells observed at time point t. Panel F: Number associated with the count of MTrack2 at time t+1. Note that since the fluorescent cells are tracked through time, cells should be labeled 1 and 2. However, since these cells are not clearly separated at t+1, MTrack2 fails to detect that they continue to be the same objects as at time t. Consequently, MTrack2 labels this object as a new fluorescent cell, 3, thus leading to a false positive.

FIG. 12 illustrates an embodiment of the biological sample holder 1 wherein a specimen receiving chamber 50 is a cylinder for the receipt of biological samples embedded in an agar plug. The lower figure illustrates that a positive pressure, indicated by the arrow, applied to the plug will force it to partially descend from the specimen receiving chamber 50 to position the biological specimen into a light-sheet beam.

DETAILED DESCRIPTION

Figure 1A:
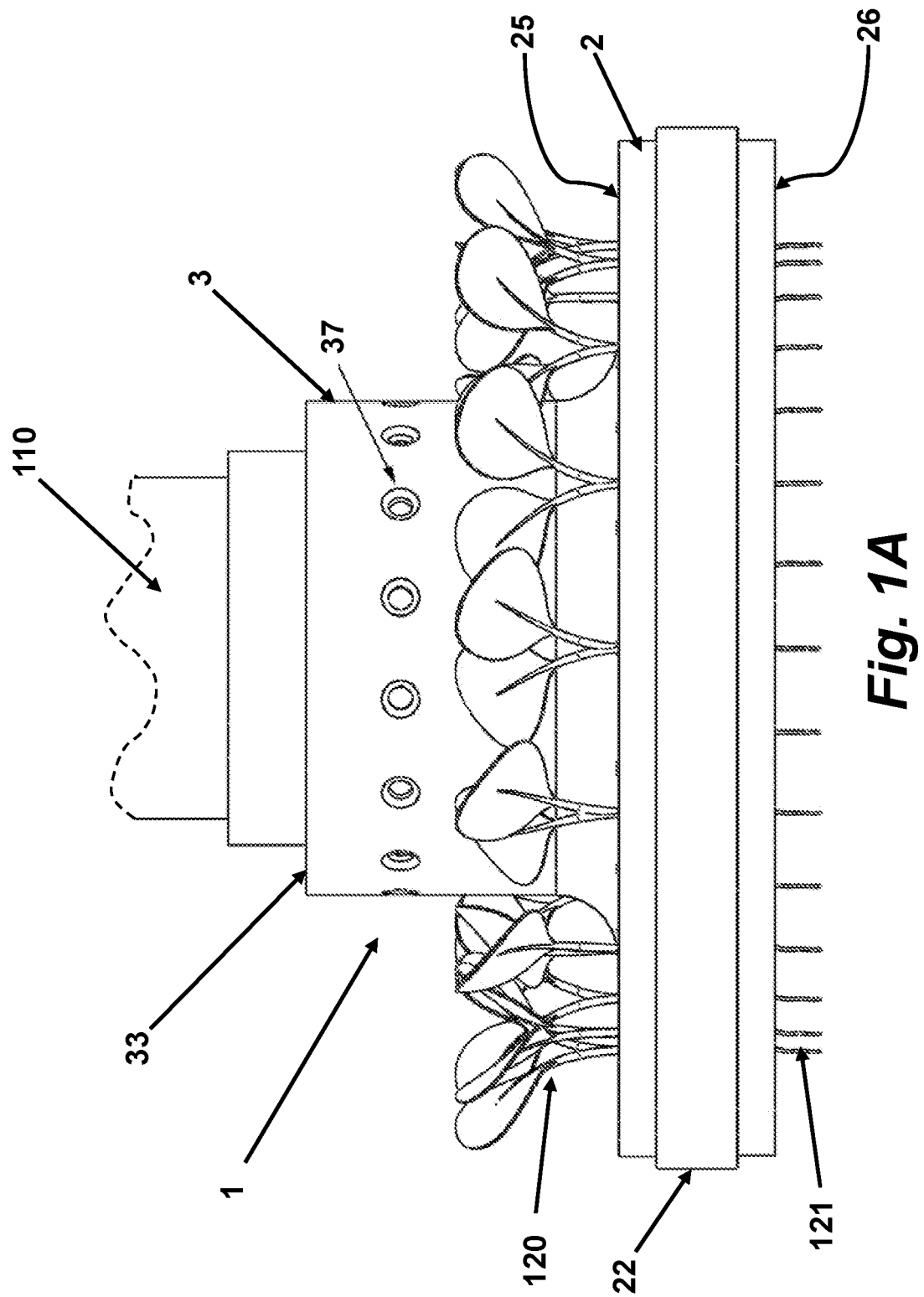
FIG. 1 is a view of an embodiment of a sample receiving disc according to the disclosure showing a plurality of plant seedlings each disposed in a sample chamber with the roots thereof descending from the bottom surface of the sample receiving disc.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

MAGIC, Multi-sample Analysis Growth and Imaging Chamber; LSFM, Light Sheet Fluorescence Microscopy; FEP, Fluorinated Ethylene Propylene Description Time-course imaging experiments on live organisms are critical for understanding the dynamics of growth and development. Light-sheet microscopy has advanced the field of long-term imaging of live specimens by significantly reducing photo-toxicity and allowing fast acquisition of three-dimensional data over time. However, current light-sheet technology does not allow the imaging of multiple plant specimens in parallel. To achieve higher throughput, a Multi-sample Analysis Growth and Imaging Chamber (MAGIC) has now been developed that provides near-physiological imaging conditions and allows high-throughput time-course imaging experiments in a light-sheet microscope such as the ZEISS Lightsheet Z.1. MAGIC's imaging capabilities could be illustrated by following cell divisions, as an indicator of plant growth and development, over prolonged time periods. To automatically quantify the number of cell divisions in long-term experiments, a FIJI-based image processing pipeline is provided and it is demonstrated that plants imaged with our chamber undergo cell divisions for at least 16 times longer than those with the manufacturer's glass capillary system such as supplied for the ZEISS Z1. However, the biological specimen holder of the disclosure is also useful for presenting a plurality of samples or specimens for observation with other microscope types including, but not limited to confocal microscopes, direct illumination microscopes, dark-ground illumination microscopes, and the like.

Limitations to LSFM remain when imaging biological specimens, especially plants. Only one specimen can be imaged at a time, the specimen to be imaged needs to be transferred and loaded from its original growing plate into an imaging capillary system, which can be time-consuming and can generate a stress response in the plant. Moreover, when loaded in the capillary system provided by ZEISS for imaging, both the shoot and root are embedded in agar, which prevents the shoot from exchanging gases, inducing an extreme stress response in the plant.

To address these issues, embodiments of a plant growth chamber and imaging device compatible with the ZEISS Lightsheet Z.1 has been developed. Although initially constructed for use in the ZEISS Lightsheet Z.1, the growth chambers of the disclosure can be adapted with respect to how they engage with a rotation drive and to the dimensions suitable for a particular make or type of microscope. While other manufacturing procedures can be used to construct the devices of the disclosure, it has been found useful to generate the devices by use of a 3D printed device.

One embodiment of the Multi-sample Analysis Growth and Imaging Chamber (MAGIC) of the disclosure, as shown in FIGS. 5A-5D, allows the growth and imaging of up to four *Arabidopsis* roots during the same experiment, eliminating the need to transfer samples while scaling up the imaging process. Moreover, MAGIC allows the shoots themselves to grow outside of the agar, allowing gas exchange during the imaging process. A protocol was developed for planting, growing, and imaging *Arabidopsis* plants in MAGIC together with a semi-automatic image processing pipeline to perform the analysis of the acquired data. Using this imaging protocol, MAGIC's imaging capabilities were validated. Roots that were imaged with MAGIC undergo significantly lower levels of physiological stress than those imaged with the ZEISS glass capillary imaging system, resulting in considerable improvements in plant development and growth in each long-term imaging session.

Figure 3:
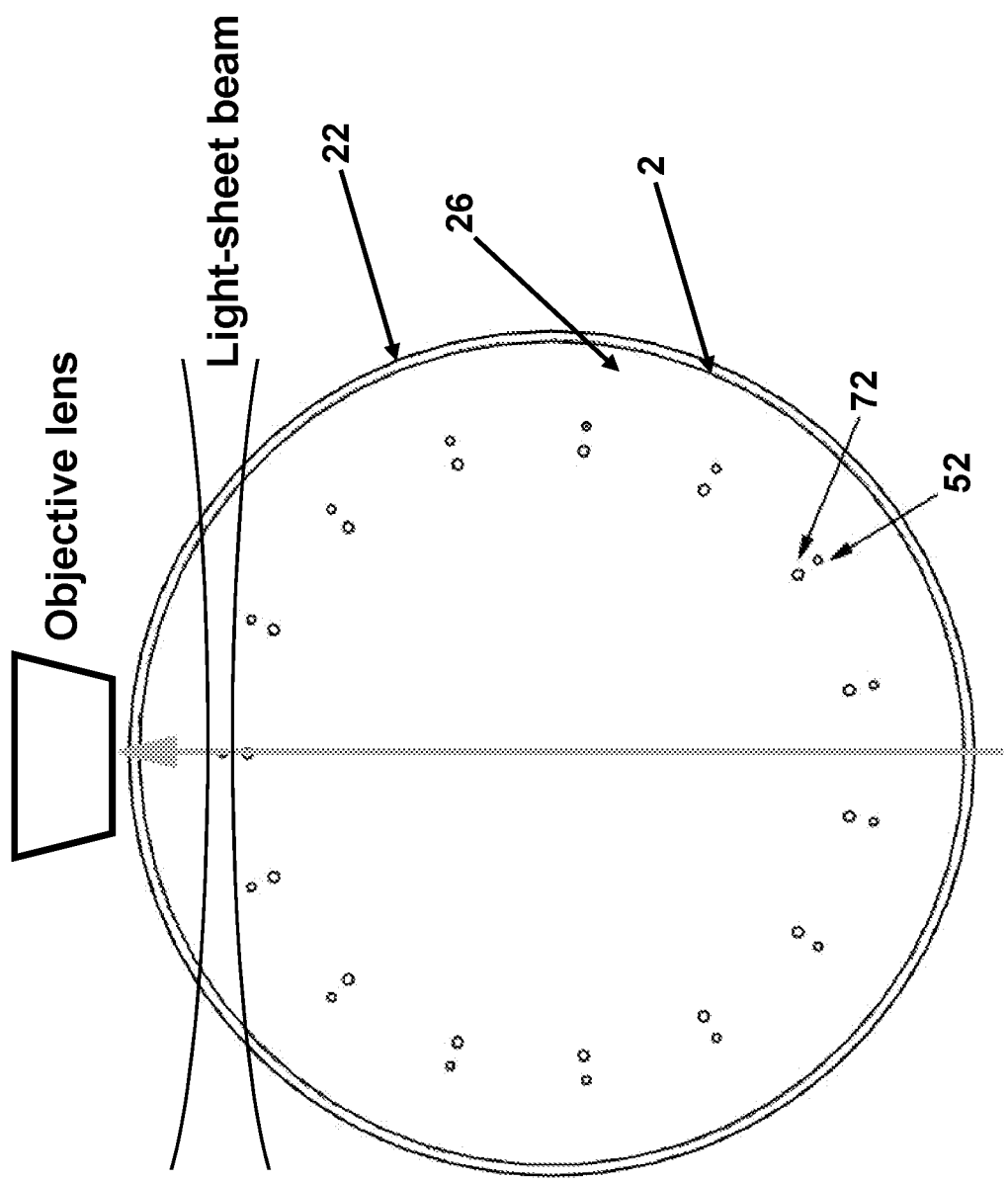
FIG. 3 is a view of the bottom surface 26 of an embodiment of a specimen receiving disc 2 of the disclosure. The arrow indicates the central axis of an objective lens observing a proximal single descending plant root. The light-sheet illuminates the specimen perpendicular to the objective lens central axis.
Figure 4A:
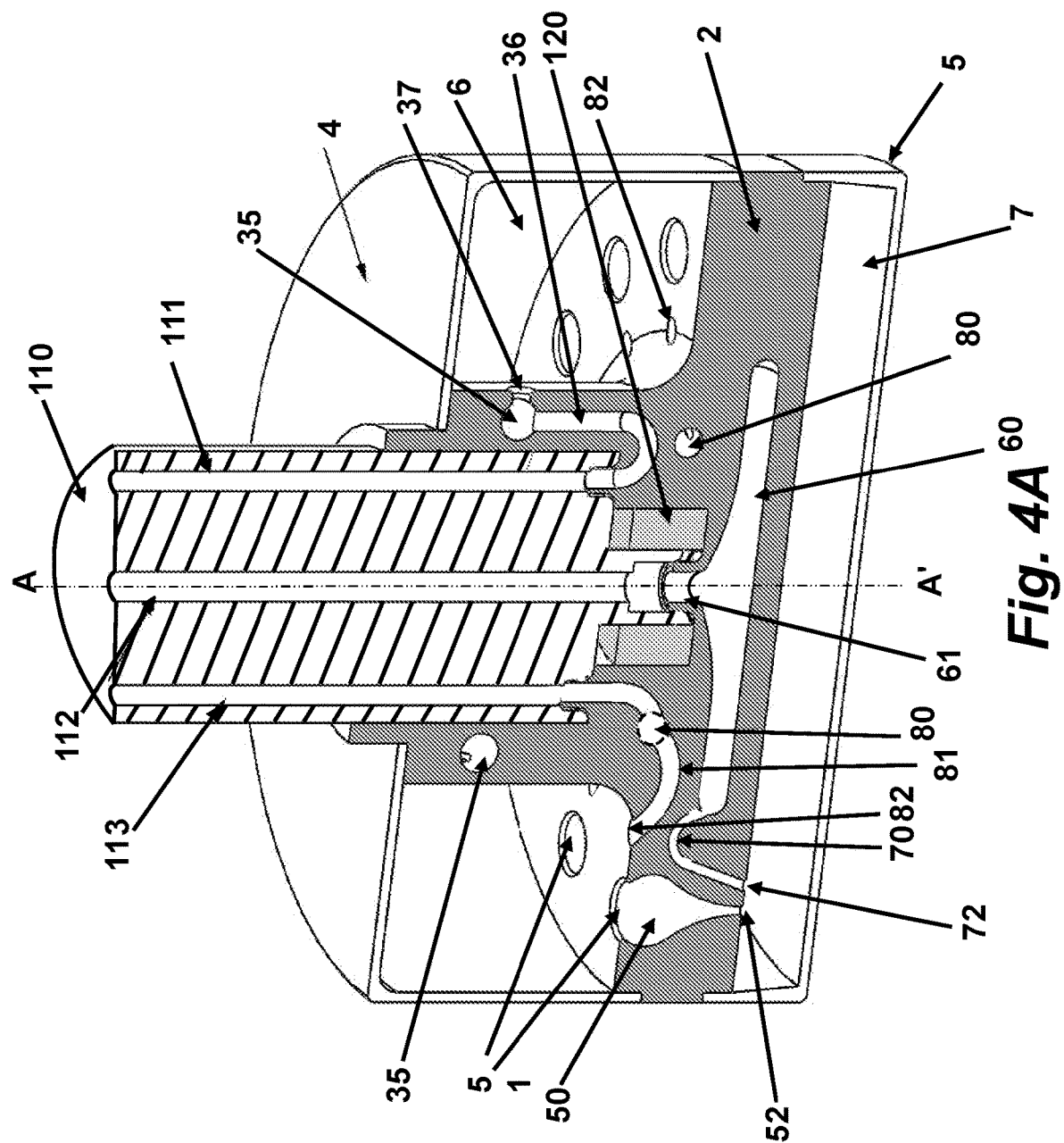
FIG. 4A is an isometric vertical section view through an embodiment of a specimen holder of the disclosure.
Figure 4C:
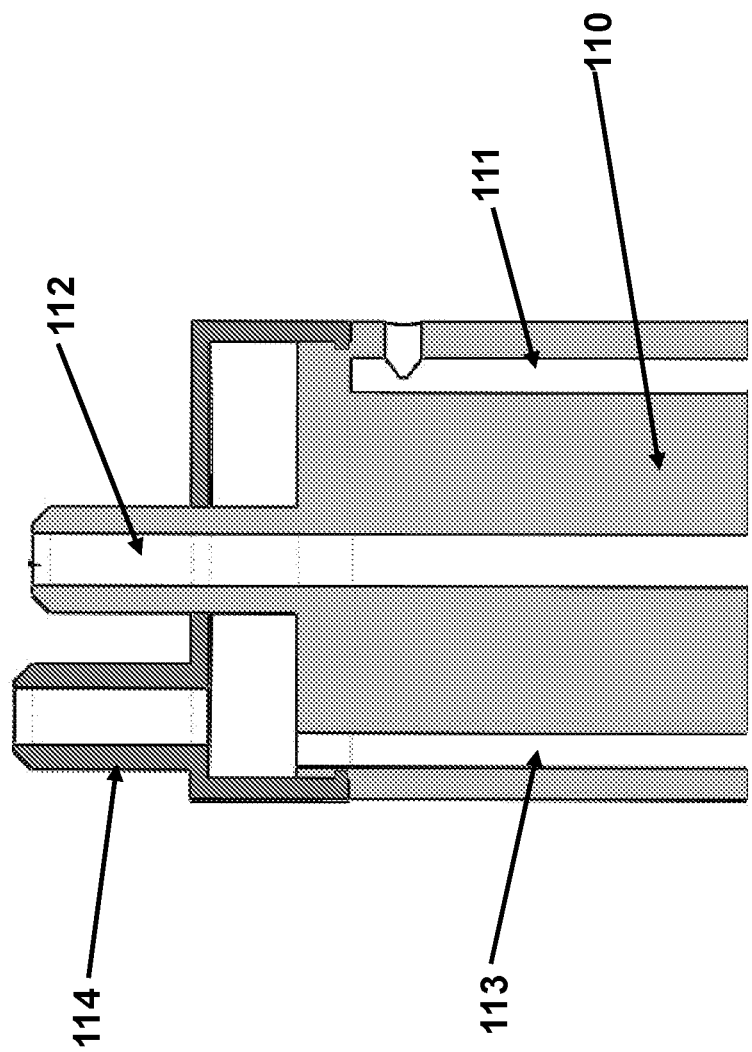
FIG. 4C is schematic of a gas inlet/outlet port arrangement at the distal end of the drive shaft 110 allowing gas exchange with the top chamber 106 through the ducts 111, 112, and 113 when the driveshaft is attached to a biological specimen body of the disclosure.
Figure 5A:
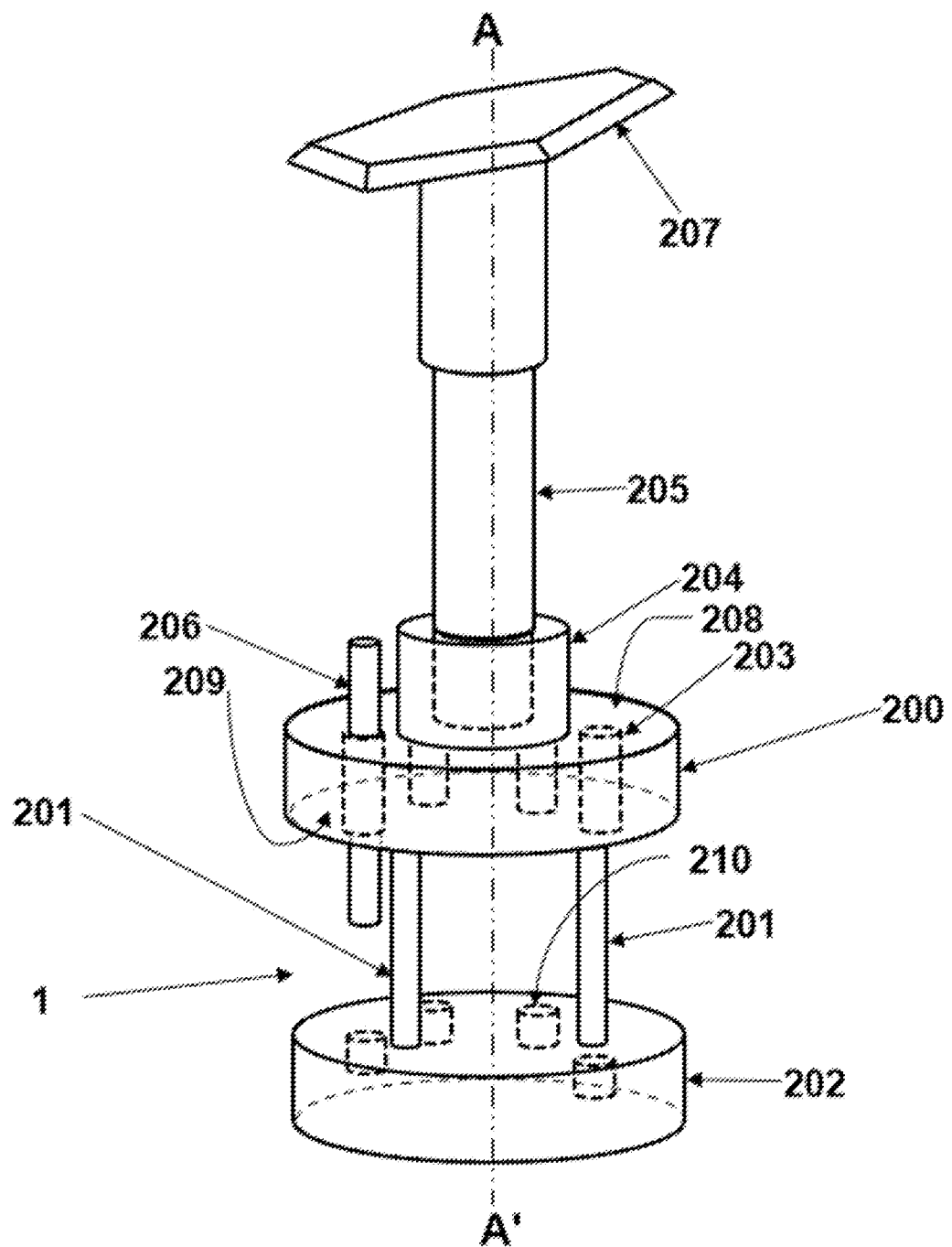
FIG. 5A is an isometric illustration of an embodiment of a specimen holder according to the disclosure.
Figure 5D:
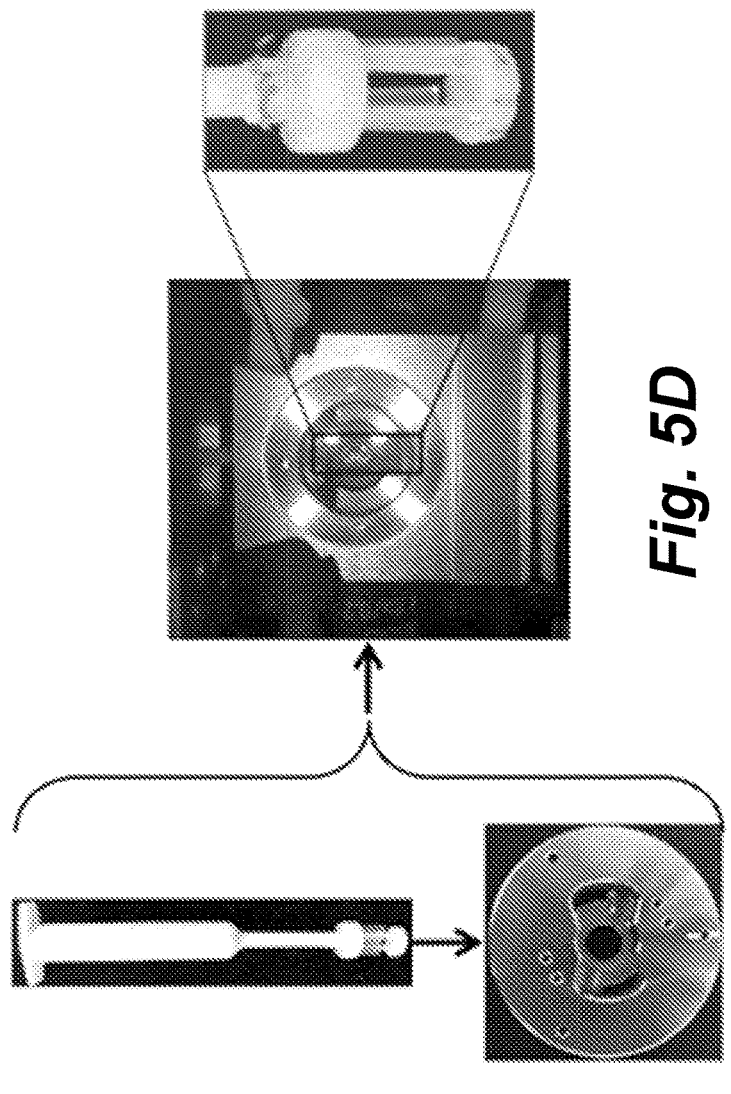
FIG. 5D is a series of digital images schematic illustrating an embodiment of the specimen holder of the disclosure mounted and locked into the metal holder of a ZEISS Lightsheet Z.1 microscope. Note that the plant sample receiving disc is visualized through the window (square). Right-hand image: zoom of the specimen holder and the plants inserted in the Z.1 and the imaging chamber filled with water.
Figure 5E:
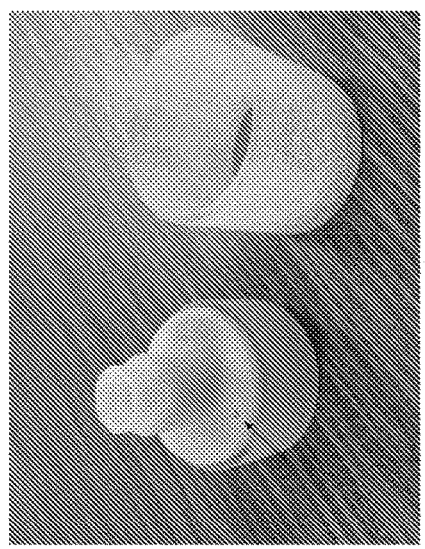
FIG. 5E is a digital image of an embodiment of the specimen holder of the disclosure showing a removable mold and top cover (not in situ).
Figure 5C:
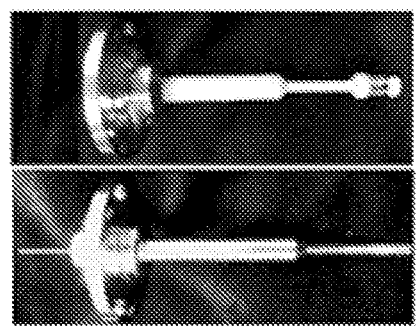
FIG. 5C illustrates digital side by side images of the ZEISS glass capillary (left) and an embodiment of a specimen holder of the disclosure (right), both mounted into the metal sample holder of the light-sheet microscope.

The MAGIC devices of the present disclosure allow growth and imaging of multiple roots in near physiological conditions, as shown in FIGS. 1-5D. The 3D printed devices of the disclosure takes advantage of the ZEISS stage setup, which allows a specimen to remain in a vertical position and enabling the plants to follow the gravity vector. Similar to the glass capillary of the Lightsheet Z.1 illustrated in FIG. 5C, MAGIC can attach to the ZEISS sample holder as shown in FIGS. 5C and 5D, and to be inserted into the microscope through the upper system cavity door.

In particular, embodiments of the specimen holder MAGIC and embodiments thereof for attaching to a light-sheet microscope comprise a drive shaft and a sample receiving disc as shown in FIGS. 1-5A. As shown in FIG. 5A, the end of the drive shaft distal to the sample receiving disc includes an attachment plate that can engage with a sample holder of the microscope, allowing MAGIC to be controlled by the ZEISS Lightsheet Z.1-associated software (ZEN Software) such that the device has the ability to move and rotate in all dimensions within a sample chamber of the ZEISS Lightsheet Z.1. It is, however, possible to provide a drive mechanism such as a belt-drive, geared drive, direct coupling to a servo motor, and the like to allow the biological sample holder of the disclosure to be usefully adapted for use in other types of microscopes to allow multiple samples to be sequentially and repeatedly observed.

The proximal end of the drive shaft engages with the sample receiving disc. By allowing plants to be placed in a circular configuration, the shape of the plant holder takes advantage of ZEN's rotational capability, granting MAGIC the ability to image multiple samples by spinning the disc around the central (vertical) axis.

In one embodiment of the devices of the disclosure, the plant-holder disc is adapted to receive from one to four Fluorinated Ethylene Propylene (FEP) specimen recipient tubes, although it is contemplated that the diameter of the sample receiving disc, the specimen recipient tubes and the positioning of each tube in the disc can allow more than four tubes to be accommodated. However, the positions of the holes are designed to individually cross the light sheet path when imaged, such that the loaded plants do not block each other or the laser paths, as shown, for example in FIG. 5B.

While not intended to be limiting, the specimen recipient tubes may be advantageously made from FEP tubes since the index of refraction of FEP (1.34) closely matches that of water (1.33) and they can be used in the Lightsheet Z.1 (Kaufmann et al., (2012) *Development* 139: 3242-3247). However, the specimen recipient tubes can be of any material that is transparent to a light-sheet and have a refractive index approximating water. Moreover, the FEP tubes allow the shoots to grow outside of the agar, permitting gas exchange during the imaging process.

The plant-holder disc, however, may be further adapted to allow the embedding of a biological specimen such as, but not limited to, a zebra fish, in a gel such as an agar gel. The gel may be formed, for example, in a perforation in the holder by first forming an agar plug in a perforation, unsolidified agar solution being held in the perforation by surface tension. The biological sample is placed in the perforation and then embedded in further agar that is allowed to gel. A syringe may be used to apply positive pressure to the top of the gel, forcing the gel to partially descend from the perforation and thus into position to be illuminated by a light beam.

Accordingly, the present disclosure encompasses some embodiments of a biological specimen holder 1 advantageous in presenting at least two biological specimens for observation by light-sheet microscopy. Referring now to FIG. 5A, illustrated is one embodiment that is configured for presenting from 1 to 4 individual plant seedling samples to a light-sheet beam for z-stack imaging of the roots thereof. In the illustrated embodiment, the biological specimen holder 1 having a vertical axis A-A' comprises a sample receiving disc 200 connected to a bottom supporting sample receiving disc 202 by at least two supporting rods 201. The sample receiving disc 200 has a top surface 208 and a bottom surface 209 and further comprises a plurality of sample tube receiving perforations 203, each of said perforations 203 traversing the thickness of the sample receiving disc 200 and each having a diameter selected to accept the insertion through the perforation of a sample tube 206 for securing therein. The bottom supporting sample receiving disc 202 may further comprise a plurality of partial perforations 210 wherein a partial perforation 210 is co-axial with a sample tube receiving perforations 203, the partial perforations being sized to receive a lower end of a sample tube 206, thereby ensuring that the sample tube 206 is aligned with the axis of the biological specimen holder 1. The sample receiving disc 200 further includes a co-axial drive shaft receiving tube 204 or, in the alternative, a co-axial indentation into the top surface 208 of the sample receiving disc 200, which is configured to securely receive and attach the sample receiving disc 200 to the proximal end of the co-axial drive shaft 205. At the distal end of the co-axial drive shaft 205 is securely connected an attachment plate 207 adapted for securing the co-axial drive shaft 205 onto a rotation drive mechanism of a light-sheet imaging microscope such as, but not limited to, a Zeiss Z-1.

A significant and novel feature of the specimen receiving disc 200 is the placement of the sample tube receiving perforations 203 such that the light-sheet beam will only encounter a single specimen tube at any one time. An illustration of such arrangement is shown in FIG. 5B showing an embodiment having four sample tube receiving perforations 203, each having a sample tube 206 inserted therein. The parallel lines indicate the extreme range of the light sheet (orthogonal to the plane of the figure) for each perforation-tube combination and that in each case only one tube can be illuminated by each of the light-sheet ranges. It is contemplated, however, that other embodiments of the specimen receiving disc 200 may have any number of desired sample tube receiving perforations 203 provided they are arranged so only one tube is illuminated by a light-sheet beam at any one time.

While it is contemplated that that the biological specimen holder 1 can be constructed as individual components 200, 201, 202, and 205 that can be securely attached to each other to provide an embodiment as shown in FIG. 5A, most advantageously the specimen holder 1 as a single entity may be formed by 3D printing as described, for example, in Example 6, below.

Figure 1B:
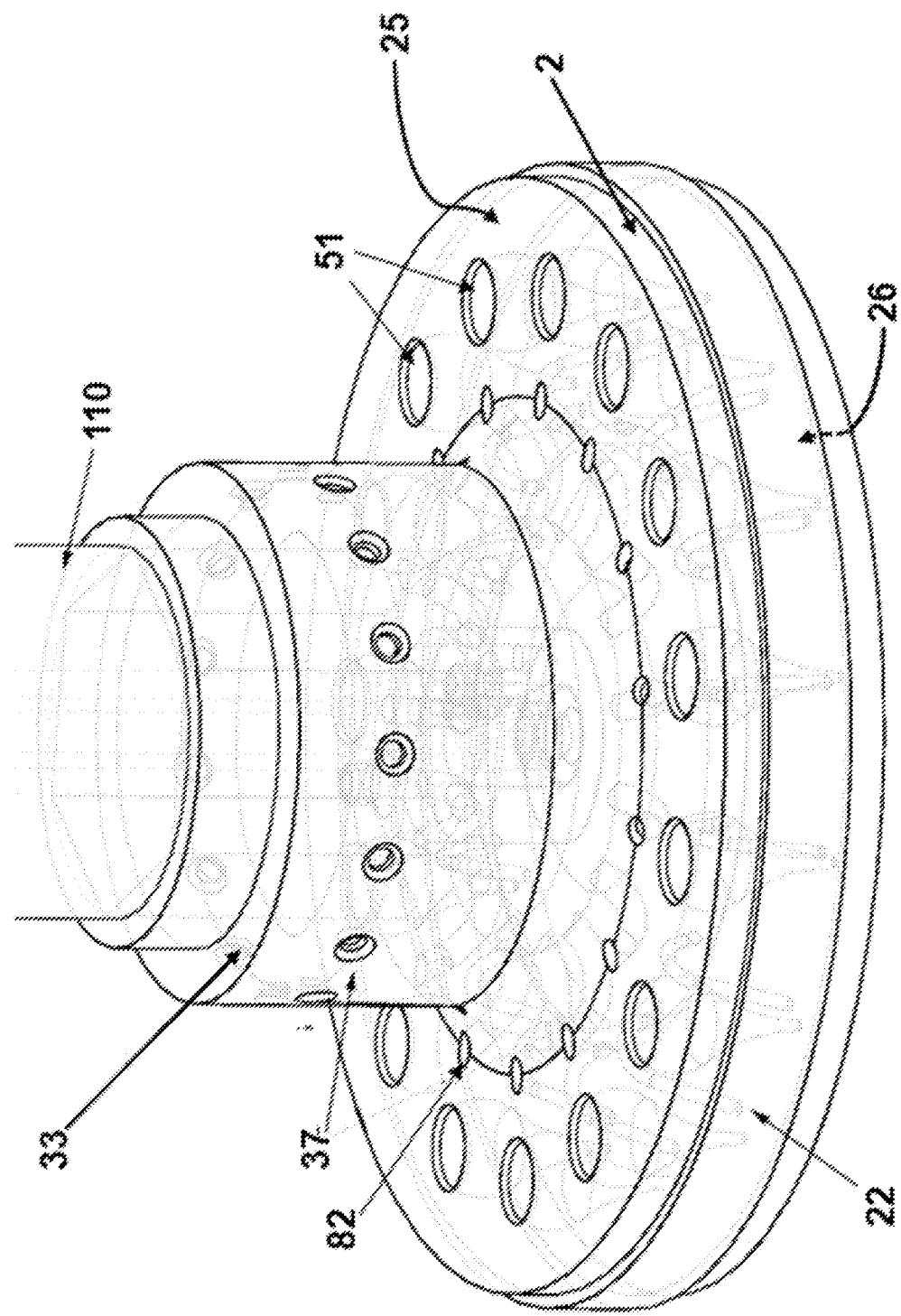

In another embodiment of the biological specimen holder 1 of the disclosure is provided a specimen holder that allows for the extended incubation of the biological specimens under constant controlled conditions of gas, liquid nutrients, light, gravity, etc. allowing for the light-sheet observations over an extended period. Referring now to FIGS. 1A and 1B, illustrated is an embodiment of a biological specimen holder 1 of the disclosure advantageous in presenting at least two biological specimens for observation by light-sheet microscopy. This embodiment comprises a sample receiving disc 2 having an annular extension 22 from the rim of the sample receiving disc 2. A co-axial tubular extension 3 can extend from the top surface 25 of the sample receiving disc 2 said co-axial tubular extension 3 having an annular shelf 33 and a plurality of gas exchange outlet ports 37 arranged around a circumference of the co-axial tubular extension 3. The top surface 25 of the sample receiving disc 2 further comprises a plurality of top openings 51 of a plurality of specimen receiving chambers 50 embedded in the sample receiving disc 2 and a plurality of gas inlet ports 82. Engaged with the specimen holder 1 by insertion into the co-axial tubular extension 3 is a co-axial drive shaft 110. Further shown in FIG. 1A are plant seedlings 120 traversing the sample receiving disc 2, with the roots 121 of the seedlings 120 extending down from the bottom surface 26 of the sample receiving disc 2.

Figure 2:
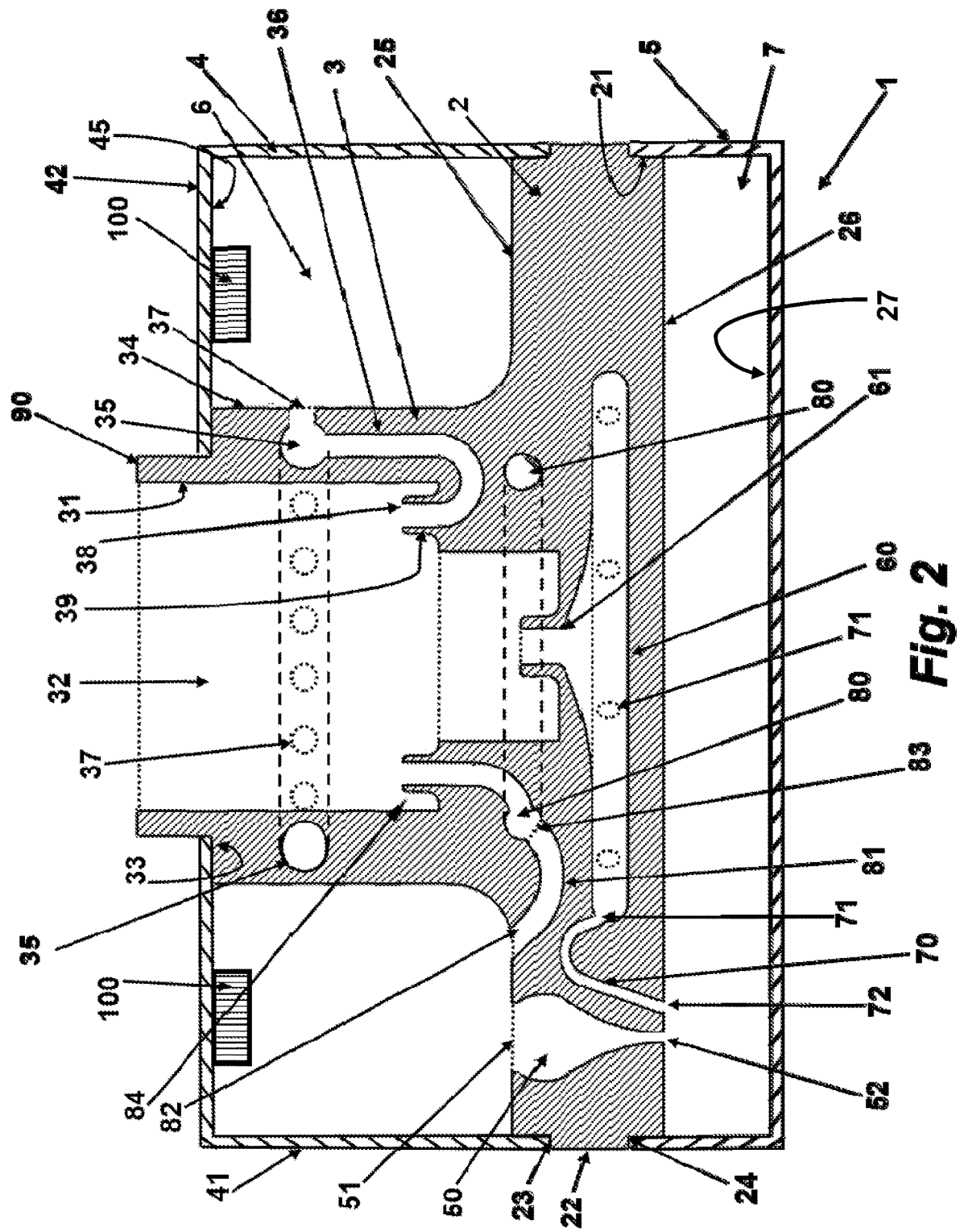
FIG. 2 illustrates a vertical section through an embodiment of the specimen holder 1 of the disclosure.

Referring now to FIG. 2, the biological specimen holder 1 of the disclosure is advantageous for presenting at least two biological specimens for observation by light-sheet microscopy. The sample holder 1 comprises a sample receiving disc 2 having a co-axial tubular extension 3. The co-axial tubular extension 3 has an inner wall 31 defining a co-axial lumen 32, wherein said lumen 32 is configured for securely receiving the proximal end of a co-axial drive shaft. The co-axial tubular extension 3 can include an annular shelf 33.

The sample receiving disc 2 of the specimen holder 1 further comprises an outer rim 21 having an annular extension 22, the annular extension 22 forming a top shelf 23 and a bottom shelf 24. The specimen holder 1 of the disclosure can further comprises a removable top cover 4 and a removable mold 5. The top cover 4 is configured to engage with the annular top shelf 23 of the annular extension 22 and onto the annular shelf 33 of the co-axial tubular extension 3. The inner surface 45 of the top cover 4, the top surface 25 of the sample receiving disc 2, and the outer surface 34 of the co-axial tubular extension 3 define a top chamber 6. Most desirably, the top cover 4 can form a gas-tight seal with the top shelf 23 and the annular shelf 33. The removable mold 5 is configured to be removably engaged with the bottom shelf 24, thereby forming a bottom chamber 7 defined by the inner surface 27 of the removable mold 5 and the bottom surface 26 of the sample receiving disc 2.

The sample receiving disc 2 of the specimen holder 1 comprises a plurality of traversing specimen receiving chambers 50, each chamber 50 having a top opening 51 in the top surface 25 of the sample receiving disc 2 and, therefore, communicating with the top chamber 6 formed when the top cover 4 is positioned on the shelves 23 and 33. Each chamber 50 also has a bottom opening 52 in the bottom surface 26 of the sample receiving disc 2 and communicating with the bottom chamber 7 formed when the bottom cover 5 is engaged with the bottom shelf 24 of the sample receiving disc 2. In some embodiments of the specimen receiving chamber 50 the chamber can be an inverted pear-shaped chamber as shown if FIG. 2.

Figure 13:
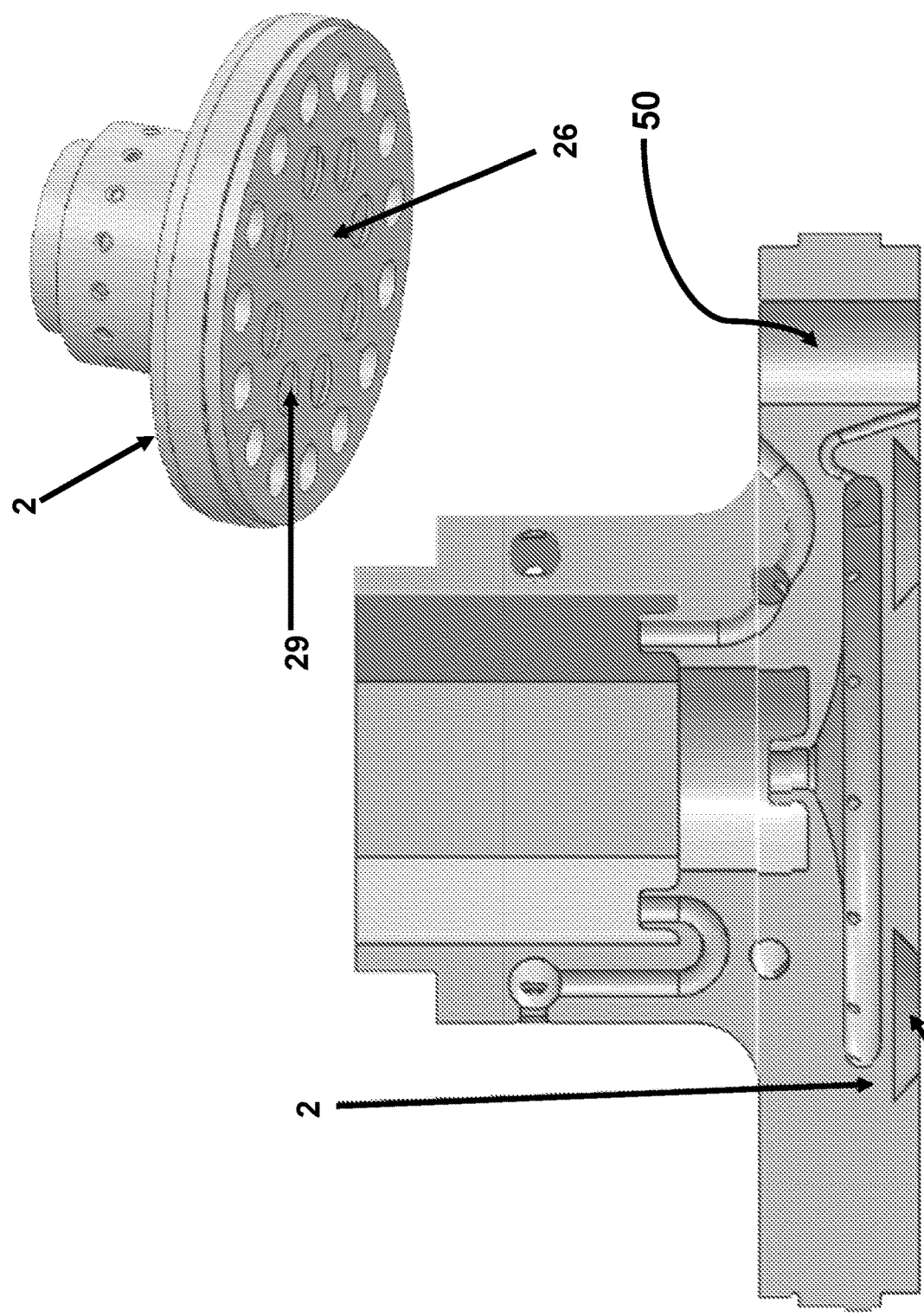
FIG. 13 illustrates a longitudinal cross-section of a sample receiving disc 2 having a plurality of negative indentations in the bottom surface 26 of the sample receiving disc 2 for securing an agar or agarose gel to the bottom surface 26.

In other embodiments of the specimen receiving chamber 50, the chamber can be a cylinder having a uniform diameter as shown in FIGS. 12 and 13. While preferably such a cylindrical chamber can have a central axis parallel to the central axis A-A' of the sample receiving disc 2, it is also possible for the cylindrical chamber can have a central axis at an angle to the central axis A-A' of the sample receiving disc 2. Cylindrical specimen receiving chambers 50 can receive an agar or agarose gel embedding a biological sample such as, but not limited to, a zebrafish embryo for examination by light-sheet illumination. As shown in FIG. 12, for example, the gel plug may be formed in situ. In one such procedure a lower gel region is formed and allowed to set, the biological sample is placed on the set gel and then surrounded with further gel solution that is allowed to set to a gel. Alternatively, the gel with the suspended biological sample may be formed externally, trimmed to the internal diameter of the specimen receiving chamber 50 and inserted therein. A positive air pressure that can be applied, by using such as a syringe inserted into the opening 51, to the top of the gel forces the gel to descend and partially extend from the bottom surface 26 of the sample receiving disc 2, thereby positioning the biological sample in the light-sheet beam. It is further contemplated that the sample receiving disc 2 of the specimen holder 1 can be manufactured using a polymer plastic that allows transmittal of a light beam to a biological sample retained in the specimen receiving chamber 50 as, for example, when embedded in a transparent or translucent gel within the specimen receiving chamber 50 and not partially descended below the bottom surface 26 of the sample receiving disc 2.

Each specimen receiving chamber 50 is disposed within the sample receiving disc 2 such that when one chamber and especially the biological specimen located in the chamber and desired to be subject to a light-sheet beam, is positioned in the beam, no other specimen receiving chamber 50 or biological sample therein is also in the illuminating light-sheet beam.

As shown in FIG. 13, embodiments of the sample receiving disc 2 may further comprise a gel securing means to securely attach a gel to the bottom surface 26 after the removable mold 5 has been removed from the sample receiving disc 2. Said gel securing means can comprise a plurality of negative-angled indentations or protuberances 29, respectively in or on the bottom surface 26 of the sample receiving disc 2 and which, when a gel is formed in the bottom chamber 7, secure the gel by its resting on the negative-angled indents or protuberances. Most preferably, the means to securely attach a gel to the bottom surface 26 are indentations to avoid any interference with an illuminating light-sheet or the resulting image. While the illustration in FIG. 13 shows circular indentations 29, any other possible opening form can be used including square, octagonal and the like.

The sample receiving disc 2 can further comprise a liquid exchange inlet mixing chamber 60 communicating with the co-axial lumen 32 of the co-axial tubular extension 3 through a projecting liquid exchange inlet connector 61. A plurality of circumferentially-arranged liquid delivery ducts 70 extend from the liquid exchange inlet mixing chamber 60. Each liquid delivery duct 70 has an inlet port 71 communicating with the inlet mixing chamber 60 and a liquid exchange inlet 72 opening into the bottom surface 26 of the sample receiving disc 2. Most advantageously, each of the liquid exchange inlets 72 is located adjacent to a bottom openings 52 of a specimen receiving chamber 50 as shown, for example, in FIG. 3. Nutrient liquids may then be passed from the liquid exchange inlet mixing chamber 60 through a liquid delivery duct 70 to a plant root descending from the bottom opening 52 of the adjacent specimen receiving chambers 50.

The co-axial tubular extension 3 includes an annular outlet duct 35 formed as an annular tubular void embedded within the wall of the co-axial tubular extension 3 and having a plurality of gas exchange outlet ports 37 opening into the top chamber 6 formed when the top cover 4 is positioned on the shelves 23 and 33. A gas outlet duct 36 operably communicates with the annular outlet duct 35 and has a second port 38 operably communicating with the lumen 32 of the co-axial tubular extension 3 via a gas exchange outlet connector 39 projecting into the lumen 32.

The sample receiving disc 2 further comprises an co-axial annular gas duct 80, formed as a circular tubular void within the body of the sample receiving disc 2, having a plurality of gas delivery ducts 81 operably communicating with the co-axial annular gas duct 80 and the top chamber 6 formed when the top cover 4 is positioned on the shelves 23 and 33, each gas delivery duct 81 having an gas inlet port 82 communicating with the surface 25 of the sample receiving disc 2 and in close proximity to a specimen receiving chamber 50, as shown for example in 4. The co-axial annular gas duct 80 further includes a gas inlet duct 83 projecting into the lumen 32 of the co-axial tubular extension 3 via a gas exchange inlet connector 84 projecting into the lumen 32

The top cover 4 comprises a circular descending wall 41 and a top plate 42 attached thereto, said plate 42 including a co-axial perforation having a diameter sufficient to receive the co-axial tubular extension 3 or an extension 90 therefrom. In some embodiments of the device of the disclosure, a plurality of LED lights 100 may be attached to the top cover 4 and electrically connected to power source to provide an illuminating light suitable for the growth of a biological specimen such as a plant.

Referring to FIG. 3, shown is the bottom surface 26 of an embodiment of the sample receiving disc 2. The bottom opening 52 of each of a plurality of specimen receiving chambers 50 located within the body of the sample receiving disc 2 is positioned such that no two bottom openings 52 are located on the same diametric plane such as indicated by the arrow in FIG. 3. The plurality of bottom openings 52 are preferably arranged in a circle concentric with the vertical axis A-A' of the sample receiving disc 2, as shown in FIG. 4.

Referring now to FIG. 4A, the biological specimen holder 1 of the disclosure can be secured to a co-axial drive shaft 110 that has a proximal end 114 and a distal end 115. Said proximal end is configured to be securely inserted into the lumen 32 of the co-axial tubular extension 3 of the specimen holder 1. For example, but not intended to be limiting, the diameter of the proximal end 114 of the drive shaft 110 and the diameter of the lumen 32 may be engineered to provide sufficient gripping force to prevent the specimen holder 1 from detaching from the end of the drive shaft 110 during observations on the biological samples. In one embodiment, as shown in FIG. 4A, magnets 120 may be included in the lumen 32 to hold the drive shaft 110 if the latter is made of a magnetic material. In another embodiment, the internal wall of the co-axial tubular extension 3 is hexagonal and can engage with a hexagonal proximal end of the drive shaft to prevent slippage of the drive shaft relative to the attached sample receiving disc 2.

Embodiments of the drive shaft 110 can comprises a co-axial liquid delivery duct 112 configured such that when the drive shaft is securely inserted into the lumen 32 of the specimen holder 1 the proximal end of the liquid delivery duct 112 is securely connected to, and communicating with, the liquid exchange inlet mixing chamber 61 of the liquid exchange inlet mixing chamber 60. The drive shaft further comprises a co-linear inlet gas duct 113 that, when the drive shaft is securely inserted into the lumen 32 of the specimen holder 1, the proximal end of the inlet gas duct 113 is securely and operably connected to the a gas exchange inlet connector 84 that is operably connected to the annular gas duct 80. The drive shaft further comprises a co-linear outlet gas duct 111 that, when the drive shaft is securely inserted into the lumen 32 of the specimen holder 1, the proximal end of the inlet gas duct 111 is securely and operably connected to the gas duct 35.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

MAGIC Yields in Parallel Long-Term Imaging Experiments:

To test MAGIC's imaging capabilities 3-h time-course experiments were performed the imaging outcome with plants imaged using the ZEISS glass capillary were compared. To assess the imaging capabilities in both systems, plant cell division was used as the indicator for root growth and development. Accordingly, the cyclin B1 marker (pCYCB1;1:CYCB1;1-GFP), whose expression corresponds to the G2/M phase of the cell mitotic division, was imaged.

Figure 6:
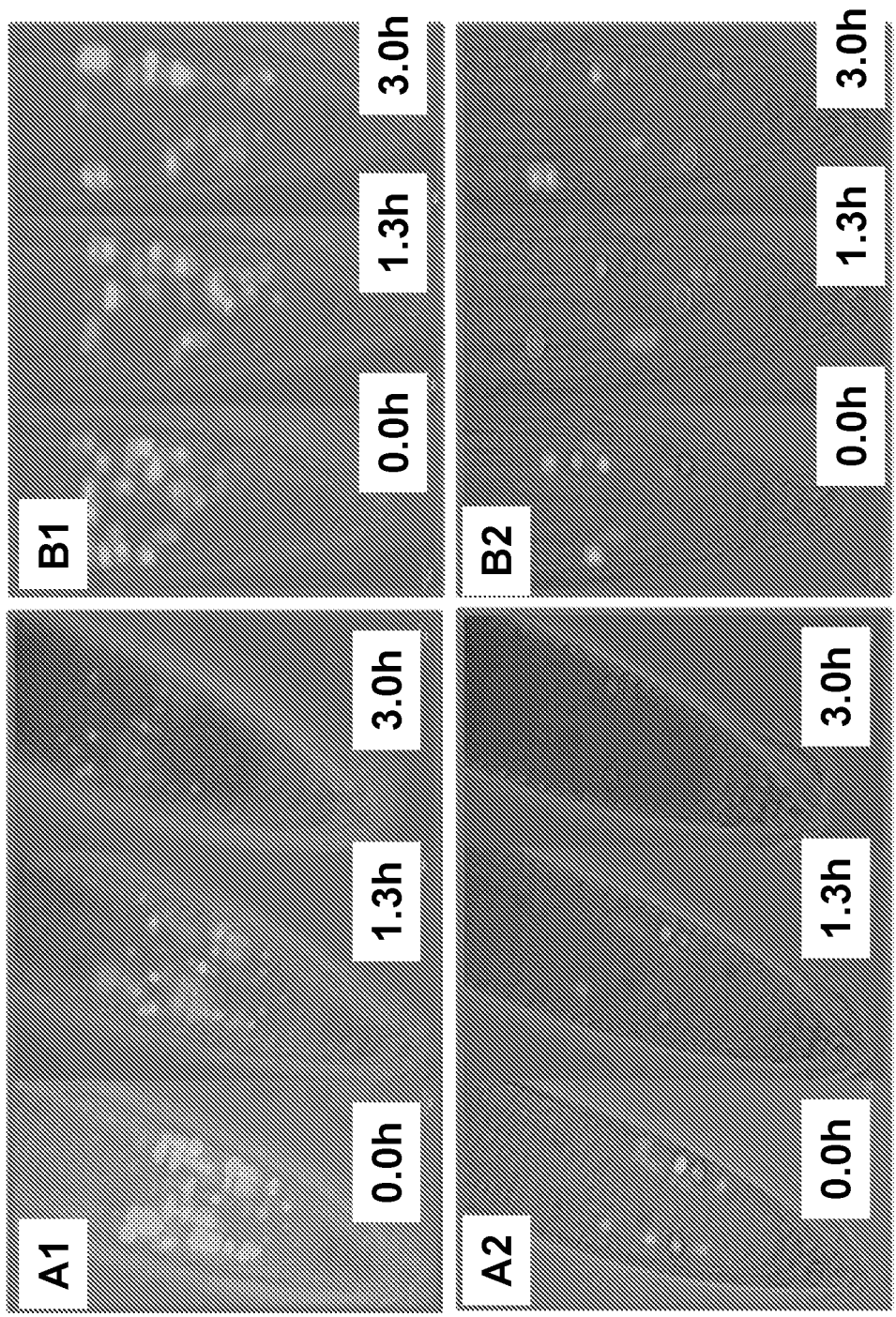
FIG. 6 illustrates light sheet images of pCYCB1;1: CYCB1;1-GFP *Arabidopsis* roots acquired every 20 min for 3 h with the original ZEISS capillary system (Panels A1 and A2) or using an embodiment of a specimen holder according to the disclosure (Panels B1 and B2). Cells expressing the CYCB1 marker correspond to dividing cells. Panels A1, B1: Max-projections (40 z-slices) of two selected roots. The projections show that cell divisions decrease during the time series using the capillary system (Panel A1) while cell divisions persist throughout the time series using MAGIC specimen holder (Panel B1). Panels A2, B2: Medial longitudinal plane of the roots shown in Panels A1 and B1. Highlighted circles depict cells that are either not progressing or progressing through the cell cycle. Through the 3-h period no new divisions are visualized in the capillary system (Panel A2), and new divisions are still observed the capillary system (Panel B2).

Using the traditional loading method of the ZEISS glass capillary system, where individual plants are transferred from a nutrient-rich plate into a glass capillary, it was observed that the CYCB1;1 marker consistently decayed within 3 h (FIG. 6-A1). Moreover, all the cells expressing the CYCB1;1 marker were still expressing CYCB1;1 from the first time point, suggesting that these divisions were arrested in the G2 phase and no new cell divisions occurred (FIG. 6-A2).

Using an embodiment of the MAGIC system of the disclosure, in which plants are grown and imaged inside of an FEP tube, ongoing cell division was observed throughout the experiment with little decay in the marker signal (FIG. 6-B1) as new cell divisions occurred at the end of the 3-h time frame (FIG. 6-B2). Moreover, with the multiplexed capacity of MAGIC, imaging 12 biological replicates required only 9 h of microscope usage, significantly reducing the length and the economic cost of the experiment compared to the 36 h required for the glass capillary system that examines single plant seedlings.

Example 2

The imaging time to 48 h (n=4 replicates) could be extended. Although at the end of this time lapse fewer cell divisions were seen, all the roots still showed the CYCB1;1 marker. By showing that plants imaged with MAGIC undergo cell divisions for at least 48 h, as opposed to approximately 3 h with the manufacturer-supplied setup, it was demonstrated that our chamber significantly improves the imaging conditions, increasing the imaging length by more than 16-fold.

Example 3

Figure 7A:
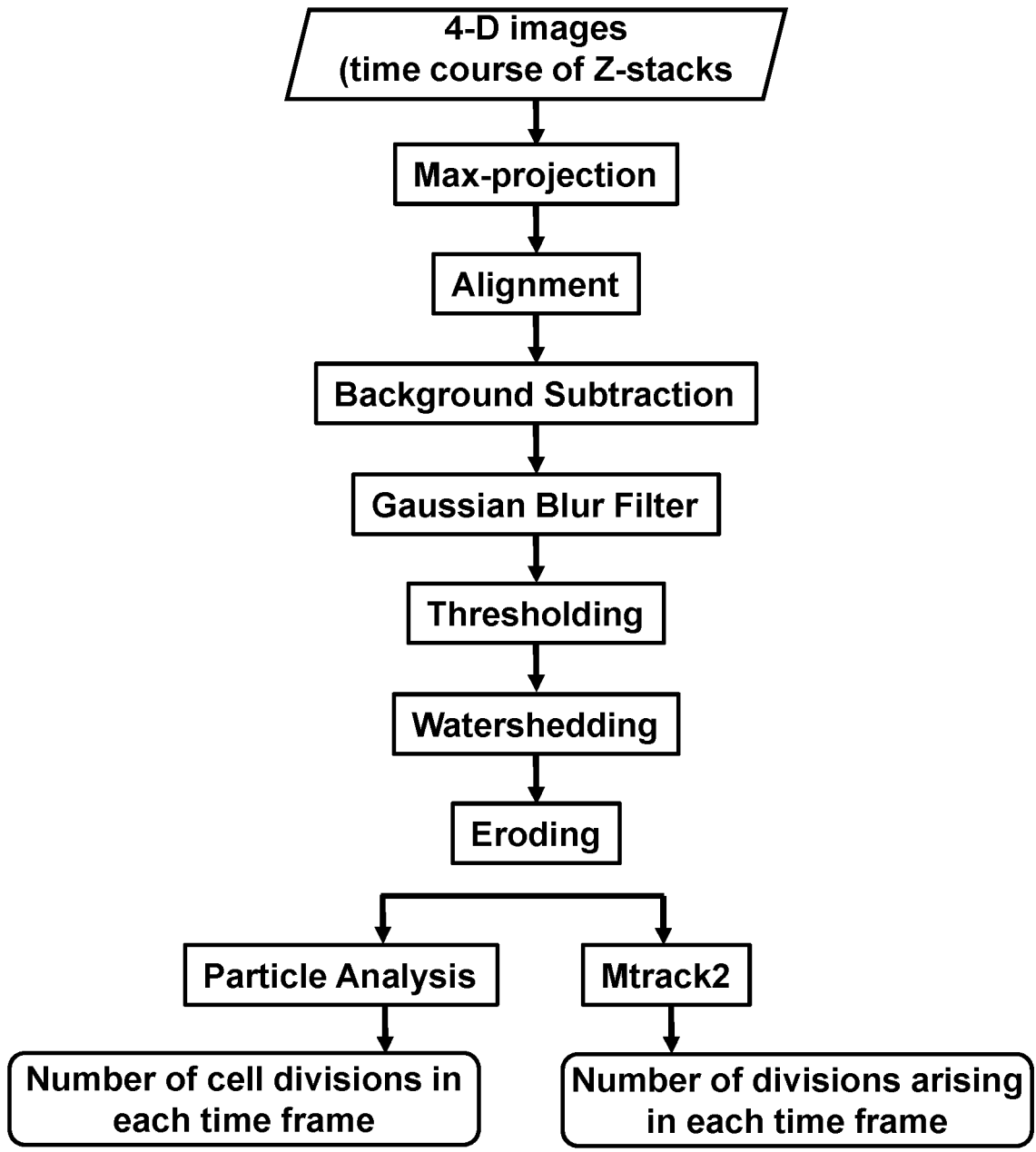
FIG. 7A illustrates a flow-chart of the image-processing pipeline in FIJI.
Figure 7B:
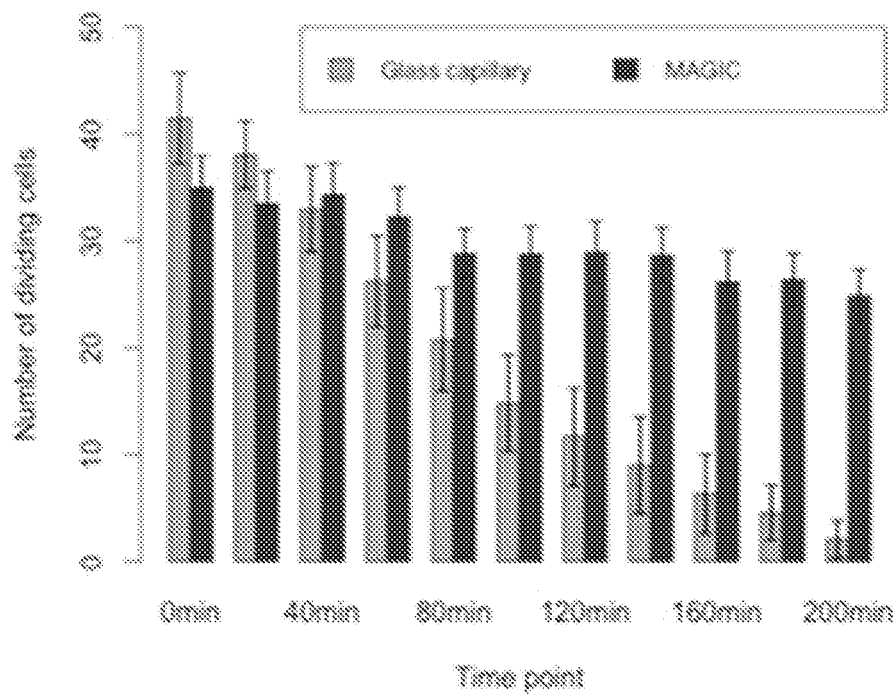
FIG. 7B is a graph illustrating the total number of cell divisions present at each time frame in the 3 h experiment in the standard glass capillary system (gray bars) and in MAGIC specimen holder (black bars).
Figure 7C:
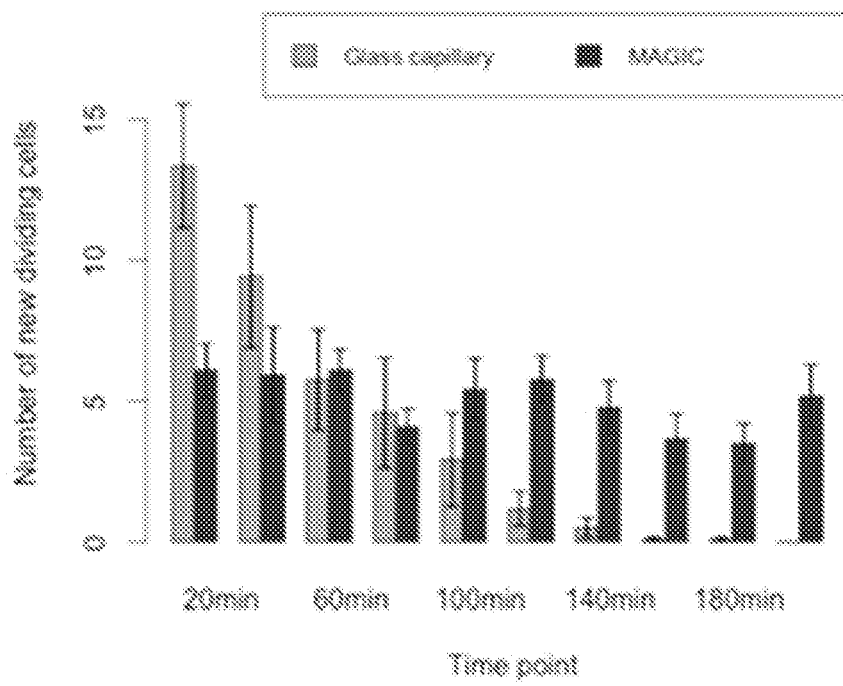
FIG. 7C is a graph illustrating the number of new cell divisions taking place at each time frame in the glass capillary system (gray bars) and in MAGIC specimen holder (black bars). Bars represent an average of the cells quantified across biological replicates in each of the imaging systems (n=12). Error bars represent the standard error of the mean values.

An Image Processing Pipeline Automates the Quantification of Cell Divisions (FIJI Image Processing Pipeline):

To evaluate whether plants would grow throughout the imaging process, the number of cell divisions that occurred during the experiments was quantified. To this aim, the number of cell divisions per time frame was also quantified as new cell divisions that are taking place at each time. The quantifications of cell divisions were automated by implementing an open-source image-processing pipeline in FIJI that incorporates built-in algorithms (FIG. 7).

For this, the z-stacks were first collapsed at each time point into a single plane by performing a maximum-intensity projection (max-projection). Since the roots grew during the experiment, the max-projections of each time course were then aligned to place the root in the same position across time. Denoising operations were subsequently applied, such as a background subtraction followed by a Gaussian Blur filter, to even the background and consequently reduce the noise. Binary images were then generated by thresholding the denoised images with thresholding algorithms.

This resulted in images with black pixels in the positions of high intensity, corresponding to the positions of the cells that were dividing. A potential drawback of thresholding is that it can miss some of the high intensity signals of an image. However, here the thresholding routines were able to identify 60-72% of the total number of dividing cells. Subsequent image processing operations, such as eroding and watershedding, separated adjacent cells and adjusted the edges of the thresholded images as needed. The format of the resulting thresholded images allowed later analysis algorithms to identify each cell as a particle, and therefore quantify both the number of cell divisions at each time frame and the new cell divisions taking place at each time.

Example 4

Quantification of Cell Divisions:

To automatically quantify, in each time frame, the total number of cells expressing the CYCB1;1 marker, the FIJI particle analysis method was applied to the binary images. The particle analysis method performed with a 9.6% chance of incorrectly labeling a new cell division (9.6% false positive rate). It was observed that an average of 19 cell divisions are taking place at each time point in the glass capillary experiment, while an average of 30 cell divisions are observed in MAGIC's experiment (FIG. 8A). In particular, the number of cell divisions observed at the end of the glass capillary experiment decreased by 94.97% with respect to the beginning of the experiment, while the decrease was only 29.06% during the imaging session performed using the MAGIC specimen holder of the disclosure.

To determine whether the CYCB1;1 expression in these experiments marked new cell divisions or cells that had become arrested in the cell cycle in the G2 phase, an algorithm was applied that could discern new cell divisions by identifying and tracking the positions of all cells expressing the CYCB1;1 marker over time. For this, Mtrack2 was applied, an available FIJI plugin that automatically tracks cells. Mtrack2 allowed us to identify when new cell divisions took place with an 8.9% chance of incorrectly labeling a new cell division (8.9% false positive rate).

Mtrack2 automatically determined that on average, the number of new cell divisions during the course of the glass capillary experiment decreased from 13 to 0 (100% decrease), suggesting that no new cell divisions occurred during the 3-h experiment (FIG. 8B). In contrast, the number of new cell divisions during the course of MAGIC's 3-h experiment decreased from 6 to 5 (15% decrease) indicating that cell divisions are constantly taking place (FIG. 7B).

Example 5

Error in the Quantification of Cell Divisions:

Image thresholding methods operate poorly when images have inadequate contrast and show variation in gray level values within the object and its background (Chen S. (2004) J. Electron Imaging 13: 220), both of which can occur when imaging Arabidopsis root with the light sheet. As a result, different intensities in CYCB1 affected the thresholding operations by generating inadequate contrast or variation in gray levels, which introduced two types of error in our analysis pipeline.

First, the variation in gray levels was mainly introduced by the difference in intensities of the cells expressing the marker. This difference in intensities resulted in the thresholding routine failing to detect the dim fluorescent cells. To estimate the percentage of all the cell divisions that the FIJI-implemented thresholding methods detected, the total number of fluorescent cells were manually counted throughout each experiment. The local thresholding method was determined able to identify 78% of the cell divisions, while the global thresholding method could identify 60% of the cell divisions.

Second, the lack of contrast was caused by insufficient signal sharpness of the pixels surrounding brightly fluorescent cells, which complicated the distinction of the edge between two or more adjacent fluorescent cells, occasionally resulting in a single thresholded object. Consequently, the tracking plugin and particle counting algorithms led to the count of extra cell divisions (false positives) (FIG. 8). By manually counting the total number of fluorescent cells occurring in the original images, it was found that an average of 9.6% of false positives was introduced by the particle analysis method, while an average of 8.9% of false positives was introduced by the tracking plugin.

Example 6

MAGIC Design and Print:

The three dimensional geometry of the chamber was designed using SOLIDWORKS® (V 2014/2015 SP3), a Computer-Aided Design (CAD) software. The native Solidworks file format was converted into the standard tessellation language (.stl) format using the highest resolution settings available in Solidworks. The chamber was fabricated with material jetting additive manufacturing (ASTM F2792) using an Objet Connex 350 (Stratasys inc.) PolyJet™ printer.

The printer functions by selectively depositing thin layers of acrylic-based photopolymer (approximately 16 µm thick), representing the cross sectional geometry of the component, which are cured by an ultraviolet light source immediately after deposition. The printer bed lowers the thickness of a single layer and the process repeats for the next cross section. STRATASYS VEROWHITEPLUS® photopolymer was used to produce the chamber.

The Connex 350 printer was prepared using standard setup, cleaning and operation protocols described by the manufacturer. As is typical of polymer-based additive manufacturing, all downfacing surfaces were supported by a secondary material, in this case OBJET SUPPORT 705®. Parts were fabricated with the "matte" setting selected in the Connex setup software in order to ensure a homogenous surface finish. A high pressure waterjet station (Stratasys) was used to remove the supporting material from the chamber after printing and, a 1.55 mm drill bit was used to manually remove support structure from the chamber seed wells to accommodate the FEP tubing.

Example 7

Plant Material and Growth Conditions:

Prior to plating, Arabidopsis CYCB1;1:CYCB1;1-GFP seeds (Doerner et al., (1996) Nature 380: 520-523) were dry sterilized using 100% bleach and 1.5 mL of HCl for at least 1 h, imbibed with 500-700 µL of sterile water, and stratified for 2 days at 4° C. in complete darkness. After stratification, seeds were plated on 1×MS (Murashige & Skooge) media supplemented with 1% sucrose and grown vertically at 22° C. in long day conditions (16 h light/8 h dark).

Seedlings were grown on square plates for 5 days when imaged with the glass capillary, while seedlings were grown in 1.55 mm thick FEP tubes (Cole Parmer, EW-06406-60) for 6 days when imaged with MAGIC. For plant growth in FEP tubes, 1×MS media was filtered with a 0.2 µm syringe filter, and 1% of low-gelling agar (Sigma number A9045-

Figure 9:
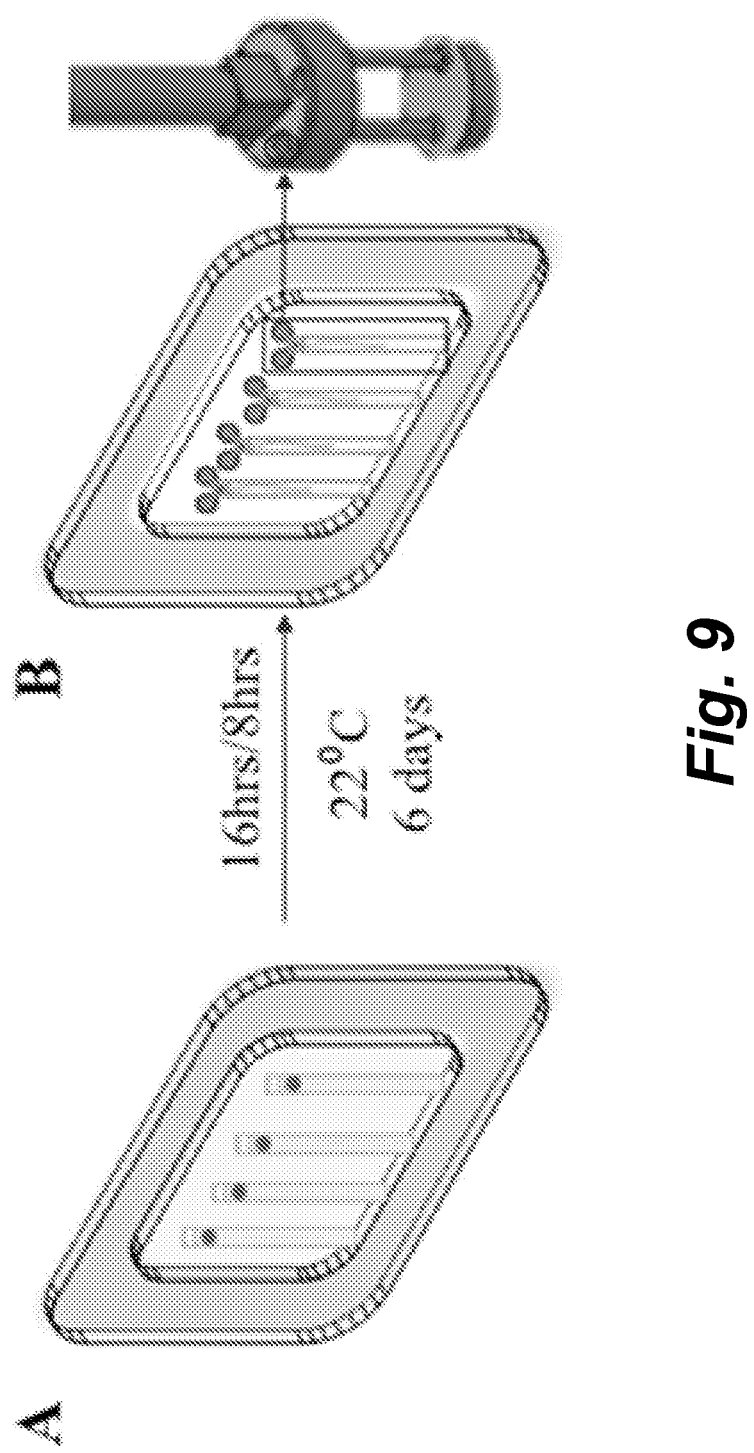
FIG. 9 illustrates a schematic of MAGIC's plating method. A: FEP tubes are filled with 20 µl of filtered 1×MS media and seeds are sowed approximately 1 mm into the agar media. Tubes are placed into a frame excavated from a 1×MS square plate and are allowed to grow. B: After six days, the FEP tubes with the grown plants are mounted into the loading positions of MAGIC, as illustrated by the blue circle. Once loaded, plants are ready to be imaged.
Figure 10:
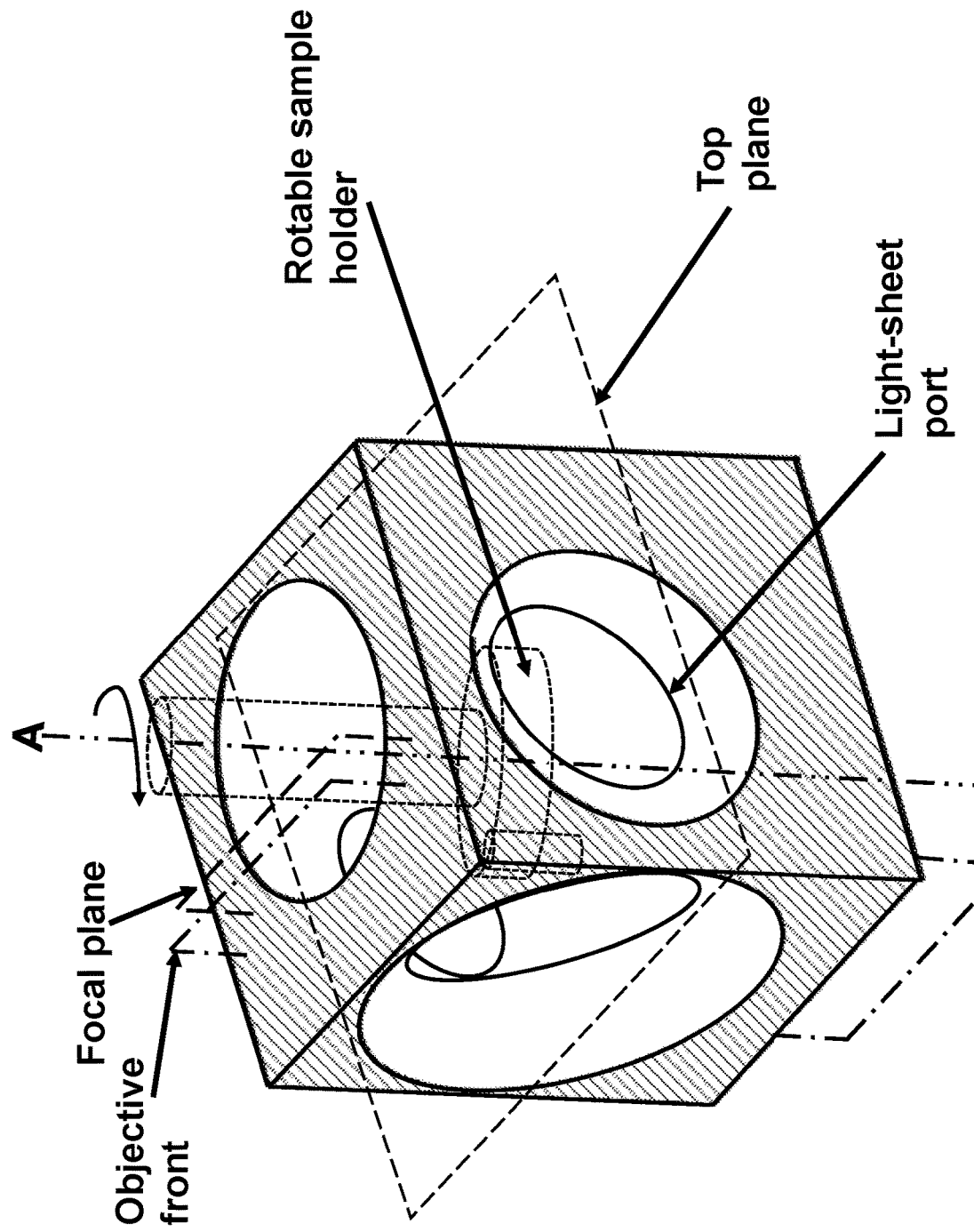
FIG. 10 illustrates an isometric view of a Zeiss light-sheet chamber enclosing a biological sample holder 1 of the disclosure. The microscope objective port of the chamber and the entry port for the illuminating light-sheet, at 90° to the central axis of the objective are indicated.
Figure 11A:
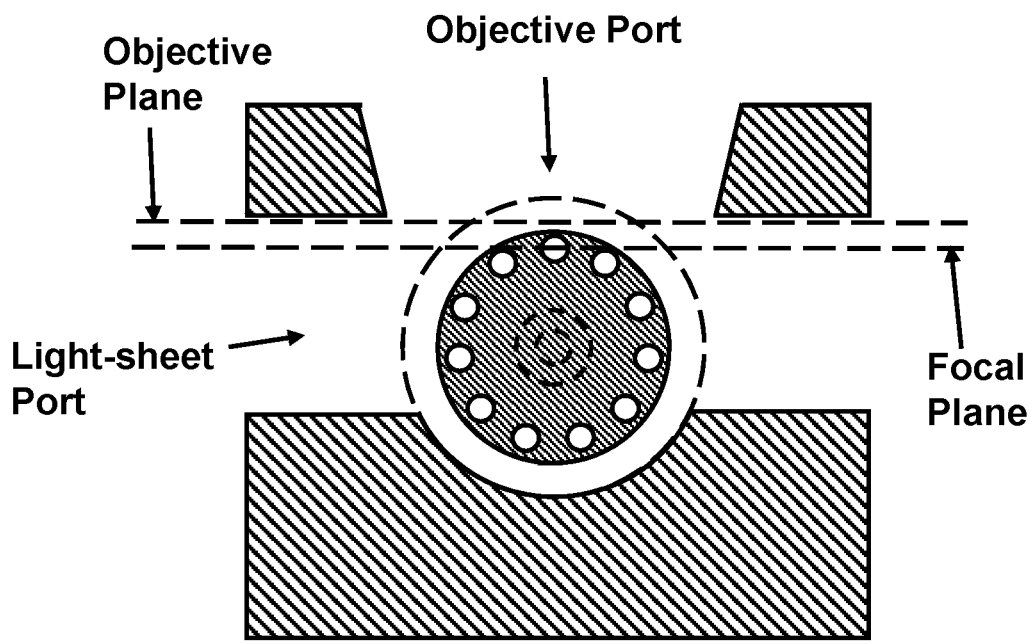
FIG. 11A illustrates a bottom view of a Zeiss light-sheet chamber and a biological sample holder of the disclosure within the chamber. Line B-B' indicates the lower limit of the front of the objective lens focused on the biological sample illuminated. Line C-C' indicates the focal plane of the objective lens imaging the sample.
Figure 11B:
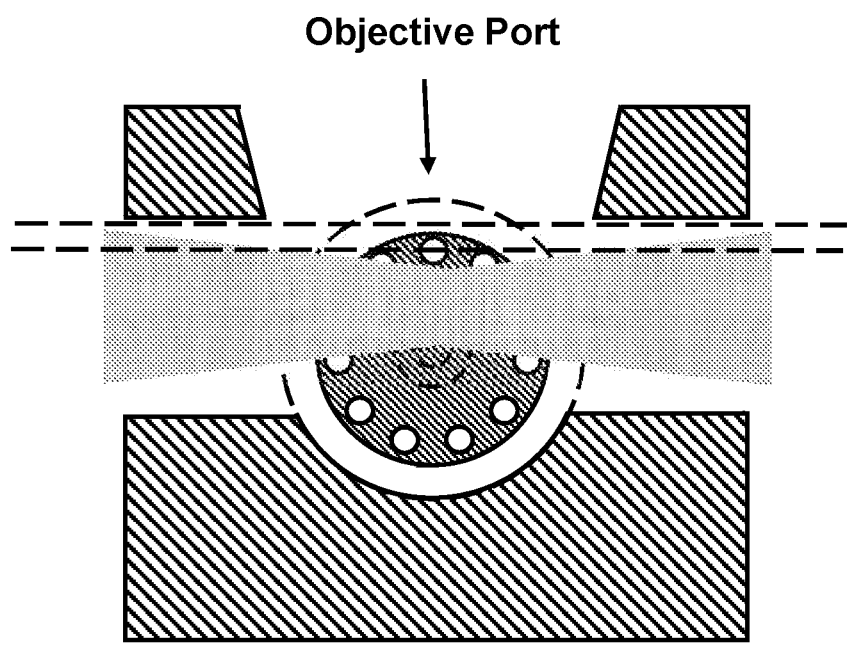
FIG. 11B illustrates a bottom view of a Zeiss light-sheet chamber and a biological sample holder of the disclosure within the chamber. Line B-B' indicates the lower limit of the front of the objective lens focused on the biological sample illuminated. Line C-C' indicates the focal plane of the objective lens imaging the sample. The light shading illustrates the light-sheet volume perpendicular to the central axis of the objective lens.

25G) was then added to the filtered solution. Sterile FEP tubes were cut to 1.5 cm lengths, and 20 μL of the filtered, sterile 1×MS 1% agar media was added to each FEP tube. The tubes were set aside for 5 min to allow for solidification. The remaining agar solution was poured into a square polystyrene plate (Genesee number 26-275) and set aside to solidify. Seeds were placed at the top of each FEP tube. Using a sterile 22-gauge syringe needle, the seeds were pushed approximately 1 mm into the agar. Once the plate had solidified completely, a sterile blade was used to cut a 2 cm window in the agar (FIG. 9). The FEP tubes containing the seeds were then vertically placed in the square hole, and the plate was sealed with Parafilm® and placed vertically in a Percival to grow. The FEP tubes in which seedlings were grown for 6 days were then placed into MAGIC prior to imaging (FIG. 9).

Example 8

Magic Imaging:

The microscope imaging chamber was filled with 20 mL of water, and allowed at least 20 min for temperature equilibration, set at 22° C. The stage was pulled down such that only the roots were submerged in water; the water level in the chamber was adjusted, when necessary. The front door camera ("Locate Capillary" tab) was used to position roots 1-4, respectively, as labeled on MAGIC, and the θ-orientation was noted for each root.

The acquisition interface was set up with the Plan-Apochromat 20×/1.0 NA water immersion detection objective lens by using the parameters specified in Table 1.

TABLE 1

| ZEISS Lightsheet Z.1 imaging parameters. | | | |
| --- | --- | --- | --- |
| Light Path and Channels Parameters | Value | Acquisition parameters | Value |
| Transmitted light | 'on' at 36% | Zoom | 1 |
| Laser | 488 nm set at 20% | Light sheet direction | single-side left |
| Laser block filter | 405/488/561 | Light sheet thickness | 4.54 μm |
| Beam splitter | SBS LP 560 | Pivot scan | 'on' |
| Camera 1 | Green (BP 505-545) | Detection module | PCO.edge |
| Camera 2 | Grey (LP 660) | Exposure time | 34.96 ms |

To conduct the experiment, the z-stack, time series, multiview, and group options were activated. A z-stack of approximately 40 slices at 3.00 μm intervals was generated for each θ-orientation and was added to the multi-view option as a new "group" (Gn corresponding to root n, for n=1, 2, 3, 4). The z-stacks for each root were taken every 20 min for at least 12 cycles. Readjustments of the root and corresponding z-stacks were made, if necessary, as it grew out of the image frame.

Example 9

Image Analysis Pipeline:

Image analysis was performed using the FIJI software. To perform the max-projection, and since the high intensity of the initial z-planes often masked the signal of the dividing cells throughout the deeper layers of the root, 15-18% of the first planes from the z-stacks had to be eliminated. The subsequent alignment of the images through time was performed with the Linear Stack Alignment using SIFT plugin with the default parameters. The next denoising operation for subtracting the background was performed using a rolling ball of 200-pixel radius, and the Gaussian Blur filter was applied with a sigma radius of 2.

Thresholding was performed with the global modified IsoData algorithm (Default method) or with the local MidGray algorithm (Parameter 1=−5). Although local thresholding methods are generally better suited for unevenly illuminated images, such as those from brightfield microscopy, global methods (modified IsoData) were chosen for the case in which the cell-tracking algorithm would be used, as this setting was found to introduce smaller errors in the tracking algorithm (Mtrack2). The particle analysis method was applied to the images that had been thresholded with the local thresholding method, with a size of 100-infinity pixels 2 and with a circularity of 0.2-1. Mtrack2 was applied to the images that had been thresholded with the global thresholding method, with a minimum object size of 1 pixel, a maximum object size of 999999 pixels, a maximum velocity of 10, and a minimum track length of 1 frame.

We claim:

1. A biological specimen holder comprising:
a sample receiving disc having a top surface and a bottom surface, wherein the top surface has attached thereto a co-axial drive shaft receiving tube or a co-axial indent configured to receive an end of a drive shaft, and wherein the sample receiving disc has a plurality of sample tube receiving perforations arranged in a circle co-axial to the sample receiving disc, wherein each of the sample tube receiving perforations is configured to securely receive a sample tube inserted therein, and wherein the sample tube receiving perforations that are arranged in a circle co-axial to the sample receiving disc are distanced from each other so that a light-sheet beam directed through one sample tube inserted in a sample tube receiving perforation is not incident on a sample tube inserted in another sample tube receiving perforation of the sample receiving disc.

2. The biological specimen holder of claim 1 further comprising:
a bottom supporting disc having a top surface and a bottom surface; and
at least two supporting rods, one end of each of the supporting rods being attached to the bottom surface of the sample receiving disc and the opposing ends of the supporting rods being attached to the top surface of the bottom supporting disc.

3. The biological specimen holder of claim 2, wherein the bottom supporting disc comprises a plurality of perforations in the top surface thereof, and wherein each of the perforations is co-axially aligned with a perforation in the sample receiving disc.

4. The biological specimen holder of claim 2, wherein the holder is assembled from individual components, the individual components comprising the sample receiving disc, the bottom supporting disc, and at least two supporting rods.

5. The biological specimen holder of claim 1, wherein the biological specimen holder is operably connected to a light-sheet microscope, and wherein the light-sheet microscope directs a light-sheet beam to traverse only one sample tube at one time.

6. The biological specimen holder of claim 1, further comprising a drive shaft having a proximal end and a distal end, the proximal end being securely connected to the top surface of the sample receiving disc.

7. The biological specimen holder of claim 6, wherein the distal end of the drive shaft has attached a drive mechanism connector attachment plate.

8. The biological specimen holder of claim 1, wherein the holder is formed as a single structure generated by 3D printing (additive manufacturing).

* * * * *